US012559538B2

(12) United States Patent (10) Patent No.: US 12,559,538 B2
Kwon et al. (45) Date of Patent: *Feb. 24, 2026

(54) PD-1 POLYPEPTIDE VARIANTS

(71) Applicant: EUTILEX CO., LTD., Seoul (KR)

(72) Inventors: Byoung S Kwon, Seoul (KR);
Seunghyun Lee, Seoul (KR); **Hanna
Lee, Seoul (KR); Jin Sung Park,** Seoul
(KR); Jin Kyung Choi, Seoul (KR);
Seung Hee Han, Seoul (KR); **Sun Woo
Im, Seoul (KR); Hyun Tae Son,** Seoul
(KR)

(73) Assignee: EUTILEX CO., LTD., Seoul (KR)

( * ) Notice: Subject to any disclaimer, the term of this
patent is extended or adjusted under 35
U.S.C. 154(b) by 0 days.

This patent is subject to a terminal dis-
claimer.

(21) Appl. No.: 17/469,549

(22) Filed: Sep. 8, 2021

(65) Prior Publication Data

US 2022/0073586 A1 Mar. 10, 2022

Related U.S. Application Data

(60) Provisional application No. 63/075,641, filed on Sep.
8, 2020.

(51) Int. Cl.
*C07K 14/705* (2006.01)
*A61P 35/00* (2006.01)
*C07K 16/28* (2006.01)

(52) U.S. Cl.
CPC ........ *C07K 14/70521* (2013.01); *A61P 35/00*
(2018.01); *C07K 16/2878* (2013.01); *C07K
2317/31* (2013.01); *C07K 2317/622* (2013.01);
*C07K 2317/76* (2013.01); *C07K 2317/92*
(2013.01); *C07K 2319/03* (2013.01); *C07K
2319/30* (2013.01)

(58) Field of Classification Search
None
See application file for complete search history.

(56) References Cited

U.S. PATENT DOCUMENTS

| | | | | |
|---|---|---|---|---|
| 2006/0134105 A1* | 6/2006 | Lazar | ................. | C07K 16/2896 |
| | | | | 424/133.1 |
| 2010/0055102 A1* | 3/2010 | Langermann | ........... | A61P 31/00 |
| | | | | 424/134.1 |
| 2018/0125934 A1* | 5/2018 | Giaccia | ................... | A61P 31/10 |
| 2018/0258177 A1* | 9/2018 | Kwon | ..................... | A61K 45/06 |
| 2018/0355039 A1* | 12/2018 | Freeman | ................ | A61P 35/00 |
| 2020/0276238 A1* | 9/2020 | Lin | ........................ | C12N 15/67 |
| 2022/0275083 A1* | 9/2022 | Kwon | ................ | C07K 16/2827 |

FOREIGN PATENT DOCUMENTS

| | | | | |
|---|---|---|---|---|
| WO | WO-2022009123 A1 * | 1/2022 | ............. | C07K 14/55 |
| WO | WO-2022149050 A2 * | 7/2022 | ............. | A61P 35/00 |

OTHER PUBLICATIONS

Lázár-Molnár et al. (PNAS Jul. 29, 2008 105(3): 10483-10488)
(Year: 2008).*
Kwon et al. (Cancer Res Jul. 1, 2021, 18(13_Suplement): Ab:
LB176) (Year: 2021).*
Notification of Transmittal of The Internal Search Report and The
Written Opinion of The International Searching Authority, or The
Declaration, filed in International Application No. PCTIB2021/
000605 dated Jan. 10, 2022.
Written Opinion of The International Searching Authority filed in
International Application No. PCTIB2021/000605 dated Jan. 10,
2022.
International Search Report filed in International Application No.
PCTIB2021/000605 dated Jan. 10, 2022.

* cited by examiner

*Primary Examiner* — Peter J Reddig
(74) *Attorney, Agent, or Firm* — Wood, Phillips, Katz,
Clark & Mortimer

(57) ABSTRACT

Provided are PD-1 polypeptide variants including an extra-
cellular domain that binds specifically to PD-L1, and a
transmembrane domain or a fragment thereof. The disclo-
sure also provides PD-1 Fc fusion proteins including an
immunoglobulin Fc region, and a PD-1 polypeptide variant.

56 Claims, 22 Drawing Sheets

Specification includes a Sequence Listing.

Fig. 1

```
        10          20          30          40          50
MQIPQAPWPV VWAVLQLGWR PGWFLDSPDR PWNPPTFFPA LLVVTEGDNA
        60          70          80          90         100
TFTCSFSNTS ESFVLNWYRM SPSNQTDKLA AFPEDRSQPG QDCRFRVTQL
       110         120         130         140         150
PNGRDFHMSV VRARRNDSGT YLCGAISLAP KAQIKESLRA ELRVTERRAE
       160         170         180         190         200
VPTAHPSPSP RPAGQFQTLV VGVVGGLLGS LVLLVWVLAV ICSRAARGTI
       210         220         230         240         250
GARRTGQPLK EDPSAVPVFS VDYGELDFQW REKTPEPPVP CVPEQTEYAT
       260         270         280
IVFPSGMGTS SPARRGSADG PRSAQPLRPE DGHCSWPL
```

Fig. 2 x 2 ug of the purified protein loaded

Fig. 5A

Standard

A(670kDa)
B(158kDa)
C(44kDa)
D(17kDa)
E(1.35kDa)

Fig. 5B

PD-1 Fc
- concentration : 0.35mg/ml
- Monomeric(%) : 91%

**PD-L1 cell binding assay
PD-L1 positive cell**

**PD-L1 cell binding assay
PD-L1 negative cell**

Fig. 8A
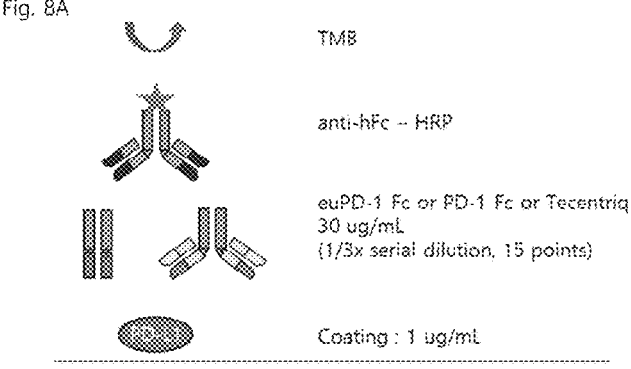
TMB
anti-hFc – HRP
euPD-1 Fc or PD-1 Fc or Tecentriq
30 ug/mL
(1/3x serial dilution, 15 points)
Coating : 1 ug/mL
Fig. 8B    Single antigen ELISA (PD-L1)
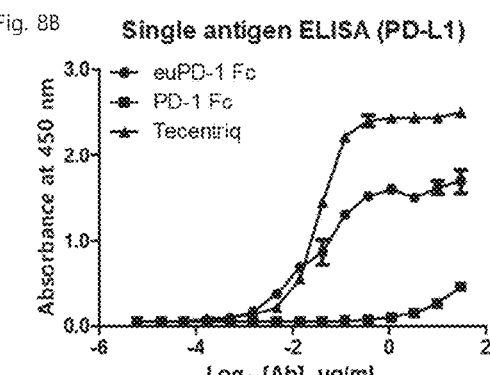
Fig. 8C
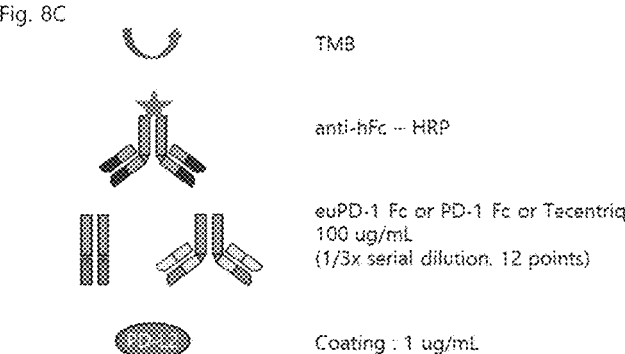
TMB
anti-hFc – HRP
euPD-1 Fc or PD-1 Fc or Tecentriq
100 ug/mL
(1/3x serial dilution, 12 points)
Coating : 1 ug/mL
Fig. 8D    Single antigen ELISA (PD-L2)
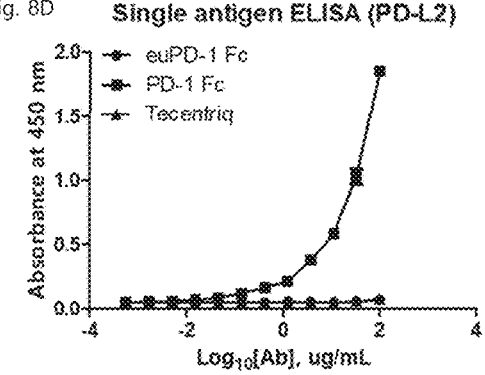

PD-L1 positive cell

PD-1/PD-L1 blockade assay

Fig. 10
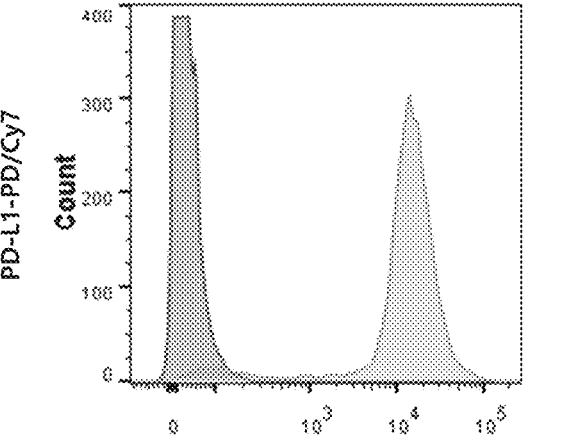
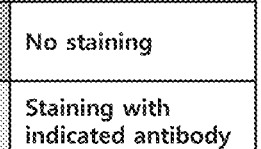

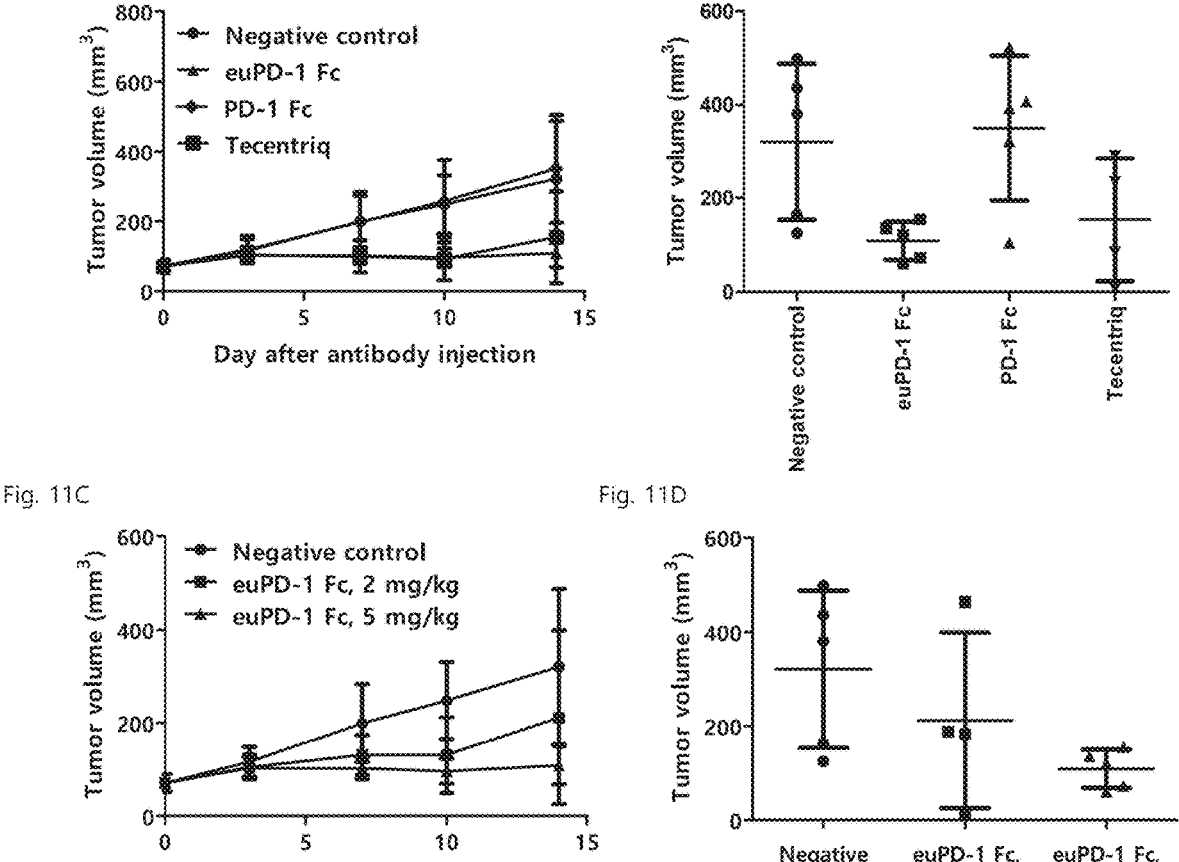

| 1. euPD-1 x 94kvt HLC 218 | 2. euPD-1.2 x 94kvt HLC 218 | 3. euPD-1 x 94kvt LHC 218 | 4. euPD-1.2 x 94kvt LHC 218 |
|---|---|---|---|
| | | | |

| PD-L1 binding | Ka (1/Ms) | Kd (1/s) | KD (nM) |
|---|---|---|---|
| euPD-1 x 94kvt HLC 218 | 1.46E+06 | 1.69E-03 | 1.16 |
| euPD-1.2 x 94kvt HLC 218 | 8.37E+05 | 1.86E-03 | 2.22 |
| euPD-1 x 94kvt LHC 218 | 1.00E+06 | 1.58E-03 | 1.58 |
| euPD-1.2 x 94kvt LHC 218 | 8.37E+05 | 1.86E-03 | 2.22 |

TMB

Avidin-HRP 4-1BB-biotin
: 1 ug/ml

BsAB
: 1 ug/ml (10x serial dilution, 3 point)

Coating : PD-L1-his 1 ug/ml

PD-1 POLYPEPTIDE VARIANTS

CROSS-REFERENCE TO RELATED APPLICATIONS

The present application claims priority to U.S. 63/075,641, filed Sep. 8, 2020, the entire contents of which are incorporated herein by reference.

BACKGROUND

Cancer remains one of the leading causes of death in the world. Recent statistics report that 13% of the world population dies from cancer. According to estimates from the International Agency for Research on Cancer (IARC), in 2012 there were 14.1 million new cancer cases and 8.2 million cancer deaths worldwide. By 2030, the global burden is expected to grow to 21.7 million new cancer cases and 13 million cancer deaths due to population growth and aging and exposure to risk factors such as smoking, unhealthy diet and physical inactivity. Further, pain and medical expenses for cancer treatment cause reduced quality of life for both cancer patients and their families.

Programmed cell death protein 1 (PD-1) is an immune checkpoint receptor with a role in regulating the immune system response by down-regulating the immune system and promoting self-tolerance by suppressing T cell inflammatory activity. Because PD-1 is overexpressed in cancer, leading to increased T-cell exhaustion and a diminished antitumor response, enhancing T cell activation by blocking the PD-1/PD-L1 inhibitory pathway has great potential for the treatment of diseases such as cancers.

SUMMARY

Provided herein are programmed cell death 1 (PD-1) polypeptide variants comprising an amino acid sequence having 95% or more sequence identity to SEQ ID NO: 4, SEQ ID NO: 6, or SEQ ID NO: 8, wherein the PD-1 polypeptide variant comprises: an extracellular domain that binds specifically to programmed cell death 1 ligand (PD-L1); and a transmembrane domain or a fragment thereof. In some embodiments, the PD-1 polypeptide variant comprises an amino acid sequence having 97% or more sequence identity to SEQ ID NO: 4, SEQ ID NO: 6, or SEQ ID NO: 8. In some embodiments, the PD-1 polypeptide variant comprises an amino acid sequence having 98% or more sequence identity to SEQ ID NO: 4, SEQ ID NO: 6, or SEQ ID NO: 8. In some embodiments, the PD-1 polypeptide variant comprises an amino acid sequence of SEQ ID NO: 4, SEQ ID NO: 6, or SEQ ID NO: 8.

In some embodiments, the PD-1 polypeptide variant comprises SEQ ID NO: 4. In some embodiments, the PD-1 polypeptide variant comprises SEQ ID NO: 6. In some embodiments, the PD-1 polypeptide variant comprises SEQ ID NO: 8.

The transmembrane domain as used in the present invention may be the wild-type transmembrane domain of PD-1 corresponding to amino acid residues 171-191 of SEQ ID NO: 11 or a fragment thereof. In some embodiments, the transmembrane domain is a fragment of the transmembrane domain including 1, 2, 3, 4, 5, 6, 7, 8, 9, 10, 11, 12, 13, 14, 15, 16, 17, 18, 19, 20, or 21 amino acid residues inclusive of all ranges and sub-ranges bound by these values. For example, the transmembrane domain fragment may comprises at least two amino acid residues, at least 5 amino acid residues, or at least 10 amino acid residues. In some embodiments, the transmembrane domain has two amino acid residues corresponding to amino acid residues 171-172 of SEQ ID NO: 11. In some embodiments, the transmembrane domain has three amino acid residues corresponding to amino acid residues 171-173 of SEQ ID NO: 11. In some embodiments, the transmembrane domain has four amino acid residues corresponding to amino acid residues 171-174 of SEQ ID NO: 11. In some embodiments, the transmembrane domain has five amino acid residues corresponding to amino acid residues 171-175 of SEQ ID NO: 11.

Included in the definition of the transmembrane domain or a fragment thereof is a variant of the wild-type transmembrane domain of PD-1 corresponding to amino acid residues 171-191 of SEQ ID NO: 11 modified by addition, deletion, substitution of one to five amino acids inclusive of the integer values of one, two, three, four, and five amino acids that may be modified, added, or substituted relative to the wild-type transmembrane domain of PD-1 corresponding to amino acid residues 171-191 of SEQ ID NO: 11.

Provided herein are programmed cell death 1 (PD-1) polypeptide variants comprising an amino acid sequence having 95% or more sequence identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139.

In some embodiments, the polypeptide variant has increased binding affinity to a PD-L1 molecule as compared to a wild-type PD-1 polypeptide. In some embodiments, the polypeptide variant has a binding affinity ($K_D$) for a PD-L1 molecule of about $1 \times 10^{-8}$ to $1 \times 10^{-10}$ M. In some embodiments, the polypeptide variant has a binding affinity ($K_D$) for a PD-L1 molecule of about $1.10 \times 10^{-9}$ M, about $1.037 \times 10^{-9}$ M, or about $7.14 \times 10^{-10}$ M.

Also provided herein are PD-1 Fc fusion proteins comprising: an immunoglobulin Fc region; and a PD-1 polypeptide variant linked by a peptide bond or a peptide linker sequence to the carboxy-terminus of the immunoglobulin Fc region, wherein the PD-1 polypeptide variant comprises an amino acid sequence having 95% or more sequence identity to SEQ ID NO: 4, SEQ ID NO: 6, or SEQ ID NO: 8. In some embodiments, the immunoglobulin Fc region comprises SEQ ID NO: 10 or SEQ ID NO: 16 or a sequence having 95% or more (e.g., 96% or more, 97% or more, 98% or more, or 99% or more) sequence identity to SEQ ID NO: 10 or SEQ ID NO: 16.

Also provided herein are PD-1 Fc fusion proteins comprising: an immunoglobulin Fc region; and a PD-1 polypeptide variant linked by a peptide bond or a peptide linker sequence to the carboxy-terminus of the immunoglobulin Fc region, wherein the PD-1 polypeptide variant comprises an amino acid sequence having 95% or more sequence identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139.

Also provided herein are Fc fusion BsAb (Bispecific antibody) comprising; an immunoglobulin Fc region; and a PD-1 polypeptide variant linked by a peptide bond or a peptide linker sequence to the N-terminus of the immunoglobulin Fc region, wherein the PD-1 polypeptide variant comprises an amino acid sequence having 95% or more sequence identity to SEQ ID NO: 4, SEQ ID NO: 6, or SEQ ID NO: 8; and a scFv for the anti-4-1BB antibody linked by a peptide bond or a peptide linker sequence to the C—terminus of the immunoglobulin Fc region, wherein the scFv for the anti-4-1BB antibody comprises an amino acid sequence having 95% or more sequence identity to an amino acid sequence comprising SEQ ID NO: 17 and 18 linked by a peptide bond or a peptide linker sequence.

Also provided herein are Fc fusion BsAb (Bispecific antibody) comprising; an immunoglobulin Fc region; and a PD-1 polypeptide variant linked by a peptide bond or a peptide linker sequence to the N-terminus of the immunoglobulin Fc region, wherein the PD-1 polypeptide variant comprises an amino acid sequence having 95% or more sequence identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139; and a scFv for the anti-4-1BB antibody linked by a peptide bond or a peptide linker sequence to the C— terminus of the immunoglobulin Fc region, wherein the scFv for the anti-4-1BB antibody comprises an amino acid sequence having 95% or more sequence identity to an amino acid sequence comprising SEQ ID NO: 17 and 18 linked by a peptide bond or a peptide linker sequence.

In some embodiments, the immunoglobulin Fc region comprises SEQ ID NO: 10 or SEQ ID NO: 16 or a sequence having 95% or more (e.g., 96% or more, 97% or more, 98% or more, or 99% or more) sequence identity to SEQ ID NO: 10 or SEQ ID NO: 16. In some embodiments the scFv for the anti-4-1BB antibody is an amino acid sequence that is at least 70% identical to SEQ ID NO: 22 or SEQ ID NO: 23.

The BsAb antibody of the present invention has decreased or no antibody-dependent cellular cytotoxicity (ADCC) and/or complement-dependent cytotoxicity (CDC) effects.

The BsAb antibody of the present invention demonstrates decreased or no hepatotoxicity.

In some embodiments, the fusion protein has increased binding affinity to a PD-L1 molecule as compared to a wild-type PD-1 polypeptide. In some embodiments, the fusion protein has a binding affinity ($K_D$) for a PD-L1 molecule of about $1 \times 10^{-8}$ to $1 \times 10^{-10}$ M. In some embodiments, the fusion protein has a binding affinity ($K_D$) for a PD-L1 molecule of about $1.10 \times 10^{-9}$ M, about $1.037 \times 10^{-9}$ M, or about $7.14 \times 10^{-10}$ M.

Also provided herein are nucleic acids comprising: a sequence encoding a PD-1 polypeptide variant, wherein the polypeptide variant comprises a sequence having 95% or more sequence identity to SEQ ID NO: 3, SEQ ID NO: 5, or SEQ ID NO: 7. In some embodiments, the nucleic acid further comprises: a sequence encoding an immunoglobulin Fc region, wherein the sequence encoding the immunoglobulin Fc region comprises SEQ ID NO: 9.

Also provided herein are expression vectors comprising any one of the nucleic acids provided herein. In some embodiments, the vector is a viral vector.

Also provided herein are pharmaceutical compositions comprising: any one of the PD-1 polypeptide variants provided herein or any one of the PD-1 fusion proteins provided herein; and a pharmaceutically acceptable carrier.

Also provided herein are methods of treating a subject, the method comprising: administering to the subject in need thereof any one of the pharmaceutical compositions provided herein, thereby treating a disease or a condition. In some embodiments, the subject has cancer. In some embodiments, the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

BRIEF DESCRIPTION OF DRAWINGS

FIG. 1 shows the amino acid sequence of the human PD-1 protein (SEQ ID NO: 11).

FIG. 2 shows the sequence alignment for wild-type PD-1 (SEQ ID NO: 2), PD-1.m7 (SEQ ID NO: 4), PD-1.m8 (SEQ ID NO: 6), and euPD-1 (SEQ ID NO: 8).

Figures 5A, 5B:
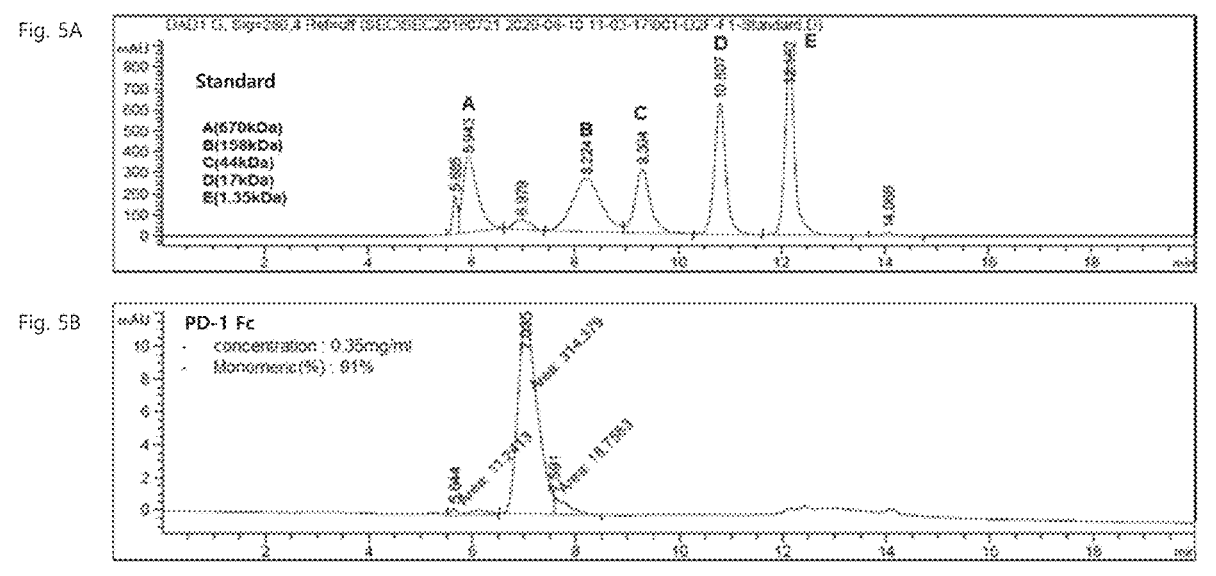

FIG. 5A-5E show a size exclusion chromatography graph with gel filtration standard (FIG. 5A), wild-type PD-1 Fc fusion protein (FIG. 5B), PD-1.m7 Fc fusion protein (FIG. 5C), PD-1.m8 Fc fusion protein (FIG. 5D), and euPD-1 Fc fusion protein (FIG. 5E).

FIG. 8A and FIG. 8C show the assay methodology of Example 7.

FIG. 8B shows binding of euPD-1 Fc fusion protein, wild-type PD-1 Fc fusion protein, and Tecentriq to antigen PD-L1.

FIG. 8D shows binding of euPD-1 Fc fusion protein, wild-type PD-1 Fc fusion protein, and Tecentriq to antigen PD-L2.

FIG. 10 shows the in vivo efficacy study control for Example 9.

FIG. 11A, FIG. 11B, FIG. 11C, and FIG. 11D show the result of tumor size observation for euPD-1 Fc and tecentriq in Example 9.

FIG. 15 shows a size exclusion chromatography graph with gel filtration standard of the Fc fusion BsAB using euPD-1 and anti-4-1BB antibody described in Example 10. Specifically.

DETAILED DESCRIPTION

Figure 3:
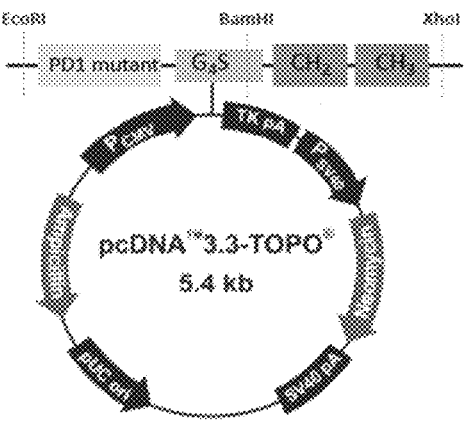
FIG. 3 shows the structure of an exemplary recombinant expression vector for PD-1 variant Fc fusion protein.

This disclosure describes variants of PD-1 polypeptides, wherein the PD-1 polypeptide variants include mutations in the wild-type PD-1 protein increasing affinity to PD-L1 molecules.

Definitions

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that are within 25%, 20%, 19%, 18%, 17%, 16%, 15%1, 14%, 13%, %12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the strength a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies, polyclonal antibodies, and fragments thereof. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE, or IgM antibodies; bi- or multi- specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody agent may lack a covalent modification (e.g., attachment of a glycan) that it would have if produced naturally. In some embodiments, an antibody agent may contain a covalent modification (e.g., attachment of a glycan, a payload [e.g., a detectable moiety, a therapeutic moiety, a catalytic moiety, etc.], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain. In some embodiments, an antibody agent is or comprises at least a portion of a chimeric antigen receptor (CAR).

Antigen: The term "antigen", as used herein, refers to an agent that binds to an antibody agent. In some embodiments, an antigen binds to an antibody agent and may or may not induce a particular physiological response in an organism. In general, an antigen may be or include any chemical entity such as, for example, a small molecule, a nucleic acid, a polypeptide, a carbohydrate, a lipid, a polymer (including biologic polymers [e.g., nucleic acid and/or amino acid polymers] and polymers other than biologic polymers [e.g., other than a nucleic acid or amino acid polymer]) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some certain embodiments, an antigen is present in a cellular context (e.g., an antigen is expressed on the surface of a cell or expressed in a cell). In some embodiments, an antigen is a recombinant antigen.

Antigen binding domain: As used herein, refers to an antibody agent or portion thereof that specifically binds to a target moiety or entity. Typically, the interaction between an antigen binding domain and its target is non-covalent. In some embodiments, a target moiety or entity can be of any chemical class including, for example, a carbohydrate, a lipid, a nucleic acid, a metal, a polypeptide, or a small molecule. In some embodiments, an antigen binding domain may be or comprise a polypeptide (or complex thereof). In some embodiments, an antigen binding domain is part of a fusion polypeptide. In some embodiments, an antigen binding domain is part of a chimeric antigen receptor (CAR).

Associated with: Two events or entities are "associated" with one another, as that term is used herein, if the presence, level, and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Chemotherapeutic Agent: The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhihitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2SN-38, hA20-SN-38, hPAM4-SN-38, hLL1-SN-38, hRS7Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-PDox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-5ME, ASG-22ME, ASG16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine.

Engineered: In general, the term "engineered" refers to the aspect of having been manipulated by the hand of man. For example, a polypeptide is considered to be "engineered" when the polypeptide sequence manipulated by the hand of man. For example, in some embodiments of the present invention, an engineered polypeptide comprises a sequence that includes one or more amino acid mutations, deletions and/or insertions that have been introduced by the hand of man into a reference polypeptide sequence. In some embodiments, an engineered polypeptide includes a polypeptide that has been fused (i.e., covalently linked) to one or more additional polypeptides by the hand of man, to form a fusion polypeptide that would not naturally occur in vivo. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, derivatives and/or progeny of an engineered polypeptide or cell are typically still referred to as "engineered" even though the actual manipulation was performed on a prior entity.

Pharmaceutical composition: As used herein, the term "pharmaceutical composition" refers to a composition in which an active agent is formulated together with one or more pharmaceutically acceptable carriers. In some embodiments, the composition is suitable for administration to a human or animal subject. In some embodiments, the active agent is present in unit dose amount appropriate for administration in a therapeutic regimen that shows a statistically significant probability of achieving a predetermined therapeutic effect when administered to a relevant population.

Pharmaceutically acceptable carrier: The term "pharmaceutically acceptable carrier", as used herein, generally has its art-recognized meaning of a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. The term "pharmaceutically acceptable carrier" may further include a pharmaceutically acceptable salt of the compound useful within the invention. Other additional ingredients that may be included in the pharmaceutical compositions used in the practice of the invention are described, for example, in Remington's Pharmaceutical Sciences (Genaro, Ed., Mack Publishing Co., 1985, Easton, Pa.), which is incorporated herein by reference. The "pharmaceutically acceptable carrier" is useful for the preparation of a pharmaceutical composition that is: generally compatible with the other ingredients of the composition, not deleterious to the recipient, and neither biologically nor otherwise undesirable. "A pharmaceutically acceptable carrier" includes one or more than one carrier. Embodiments include carriers for topical, ocular, parenteral, intravenous, intraperitoneal intramuscular, sublingual, nasal or oral administration. "Pharmaceutically acceptable carrier" also includes agents for preparation of aqueous dispersions and sterile powders for injection or dispersions.

Pharmaceutically acceptable salt: As used herein, the term "pharmaceutically acceptable salt" generally has its art-recognized meaning and refers to derivatives of the compounds provided herein wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by combining the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile may be used. Lists of suitable salts are found in Remington's Pharmaceutical Sciences, 17$^{th}$ ed., Mack Publishing Company, Easton, Pa., 1985, p. 1418 and Journal of Pharmaceutical Science, 66, 2 (1977), each of which is incorporated herein by reference in its entirety.

Excipient: As used herein, the term "excipient" generally has its art-recognized meaning and refers to physiologically compatible additives useful in preparation of a pharmaceutical composition. Examples of pharmaceutically acceptable carriers and excipients can, for example, be found in Remington Pharmaceutical Science, 16$^{th}$ Ed.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibody agents, antibody fragments, biologically active portions thereof, and/or characteristic portions thereof.

Recombinant: as used herein, is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/ or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically Effective Amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy such as a pancreatic carcinoma or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence. In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid.

Vector: as used herein, refers to a nucleic acid molecule capable of transporting another nucleic acid to which it has been linked. One type of vector is a "plasmid", which refers to a circular double stranded DNA loop into which additional DNA segments may be ligated.

Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual* 2$^{nd}$ ed., Cold Spring Harbor Laboratory Press, Cold Spring Harbor, N.Y. (1989)), which is incorporated herein by reference for any purpose. Programmed Cell Death Protein 1 (PD-1)

Programmed cell death protein 1 (PD-1) is an inhibitory receptor that is expressed by all T cells during activation. In addition to being expressed by conventional T cells, PD-1 is expressed by regulatory T cells, B cells, natural killer (NK) cells, and some myeloid cell populations. PD-1 regulates T cell effector functions during various physiological responses, including acute and chronic infection, cancer, autoimmunity, and in immune homeostasis. Further, PD-1 often shows high and sustained expression levels during antigen encounter, which can occur in the setting of chronic infections or cancer and can limit protective immunity.

In a tumor microenvironment, PD-1 and its ligand, programmed death ligand 1 (PD-L1) perform a vital role in tumor progression and survival by escaping tumor neutralizing immune surveillance. Enhancing T cell activation by blocking the PD-1 and PD-L1 inhibitory pathway has shown beneficial anti-tumor responses and long-term remissions in a subset of patients with a broad spectrum of cancers. Therefore, use of an inhibitor that blocks the interaction of PD-L1 with the PD-1 can help prevent PD-1 stimulation (e.g., on T cells), thereby increasing T cell function signals and immune cell responses.

In some embodiments, specific mutations to wild-type PD-1 are introduced to produce PD-1 polypeptide variants, wherein the specific mutations induce preferential binding to PD-L1. In some embodiments, a PD-1 polypeptide variant is a soluble PD-1 protein. In some embodiments, a PD-1 polypeptide variant comprises an extracellular domain and a transmembrane domain or a fragment thereof. The transmembrane domain or fragment thereof is described herein above.

In some embodiments, a PD-1 polypeptide variant comprises an amino acid sequence having 95% or more (e.g., 96% or more, 97% or more, 98% or more, or 99% or more) sequence identity to SEQ ID NO: 4, SEQ ID NO: 6, or SEQ ID NO: 8, wherein the PD-1 polypeptide variant comprises an extracellular domain that binds specifically to PD-L1, and a transmembrane domain or a fragment thereof. In some embodiments, a PD-1 polypeptide variant comprises an amino acid sequence of SEQ ID NO: 4, SEQ ID NO: 6, or SEQ ID NO: 8.

In some embodiments, a PD-1 polypeptide variant has increased binding affinity to a PD-L1 molecule as compared to a wild-type PD-1 polypeptide. In some embodiments, a polypeptide variant has a binding affinity ($K_D$) for a PD-L1 molecule of about $1\times10^{-8}$ to $1\times10^{-10}$ M, preferably of about $1\times10^{-9}$ to $1\times10^{-10}$ M. In some embodiments, a polypeptide variant has a binding affinity ($K_D$) for a PD-L1 molecule of about $1.10\times10^{-9}$ M, about $1.037\times10^{-9}$ M, or about $7.14\times 10^{-10}$ M.

As used herein, "nucleic acid" is used to include any compound and/or substance that comprise polynucleotides. Exemplary nucleic acids or polynucleotides can include, but are not limited to, ribonucleic acids (RNAs) and/or deoxyribonucleic acids (DNAs).

In some embodiments, a nucleic acid includes a sequence encoding a PD-1 polypeptide variant, wherein the PD-1 polypeptide variant comprises at least one of a nucleotide sequence having 95% or more (96% or more, 97% or more, 98% or more, or 99% or more) sequence identity to SEQ ID NO: 3, SEQ ID NO: 5, or SEQ ID NO: 7.

```
SEQ ID NO: 1 - human PD-1 wild type
(nucleotide sequence)
TTTTTGGATTCTCCAGACCGGCCTTGGAACCCGCCCACGTTTAGCCCTG

CTCTTTTGGTAGTTACAGAGGGGGACAACGCCACATTCACCTGCAGCTT

CTCTAATACGTCCGAGAGCTTTGTACTGAATTGGTATAGAATGAGTCCA

TCTAATCAGACAGATAAATTGGCTGCCTTCCCTGAAGACAGGAGTCAGC

CGGGTCAGGACTGCAGATTCCGCGTTACGCAACTCCCAAATGGTCGAGA

CTTTCATATGTCAGTTGTTCGGGCGAGGAGAAATGATAGCGGTACTTAC

CTGTGCGGCGCGATATCTCTCGCACCAAAAGCACAGATTAAAGAGTCTC
```

```
TCCGGGCTGAACTCCGCGTGACAGAAAGGCGAGCCGAGGTACCAACGGC

GCACCCATCACCGAGTCCTAGACCTGCGGGCCAATTCCAGACTTTGGTT

GTCGGA
```

```
SEQ ID NO: 2 - human PD-1 wild type
(amino acid)
FLDSPDRPWNPPTFSPALLVVTEGDNATFTCSFSNTSESFVLNWYRMSP

SNQTDKLAAFPEDRSQPGQDCRFRVTQLPNGRDFHMSVVRARRNDSGTY

LCGAISLAPKAQIKESLRAELRVTERRAEVPTAHPSPSPRPAGQFQTLV

VG
```

```
SEQ ID NO: 3 - PD-1 polypeptide variant PD-1.m7
(nucleotide sequence)
TTTCTGGAGTCACCCGACCGCCCTTGGAACGCACCTACCTTTTCCCCGG

CCCTCTTGCTGGTCGCAGAAGGAGATAACGCCACTTTCACATGCAGCTT

TAGTAACGCCTCCGAATCTTTTCATGTAGTTTGGCACAGAGAAAGCCCC

TCCGGACAAACCGACACCTTGGCTGCGTTTCCCGAAGACCGAAGTCAAC

CAGGGCAGGACTGCCGGTTCCGCGTAACACGGCTGCCAAACGGTAGGGA

CTTCCACATGTCAGTGGTTCGAGCACGCCGGAACGACAGCGGGACGTAT

GTCTGCGGAGTCATTAGCCTTGCCCCGAAGATACAGATTAAAGAAAGTC

TTGGGGCAGAACTTCGAGTCACCGAGCGCAGGGCCGAGGTCCCAACGGC

ACATCCCAGTCCTAGTCCACGGCCCGCCGGTCAATTTCAGACCCTTGTA

GTGGGC
```

```
SEQ ID NO: 4 - PD-1 polypeptide variant PD-1.m7
(amino acid)
FLESPDRPWNAPTFSPALLLVAEGDNATFTCSFSNASESFHVVWHRESP

SGQTDTLAAFPEDRSQPGQDCRFRVTRLPNGRDFHMSVVRARRNDSGTY

VCGVISLAPKIQIKESLGAELRVTERRAEVPTAHPSPSPRPAGQFQTLV

VG
```

```
SEQ ID NO: 5 - PD-1 polypeptide variant PD-1.m8
(nucleotide sequence)
TTTTTGGAAAGTCCCGATCGGCCTTGGAACGCTCCCACATTTAGCCCGG

CCCTGCTTTTGGTTGCTGAAGGCGATAACGCCACTTTTACATGCAGTTT

CAGCAACGCCTCTGAAAGTTTCCATGTAGTGTGGCACCGCGAGTCTCCA

AGTGGGCAAACAGATACCCTTGCAGCTTTCCCGGAAGATAGGAGTCAGC

CAGGGCAGGATCACCGGTTTAGAGTCACTCGCCTCCCCAATGGTAGAGA

TTTTCACATGAGCGTCGTTCGAGCTCAGAGAAACGATAGTGGCACATAC

GTTTGTGGCGTAATATCTCTCGCCCCGAAGATCCAGATTAAAGAGTCCC

TTGGCGCGGAGCTGAGAGTCACCGAGAGGCGAGCTGAGGTGCCTACAGC

TCATCCTAGCCCGAGCCCAAGGCCAGCTGGACAGTTCCAAACTTTGGTT

GTAGGC
```

```
SEQ ID NO: 6 - PD-1 polypeptide variant PD-1.m8
(amino acid)
FLESPDRPWNAPTFSPALLLVAEGDNATFTCSFSNASESFHVVWHRESP

SGQTDTLAAFPEDRSQPGQDHRFRVTRLPNGRDFHMSVVRAQRNDSGTY

VCGVISLAPKIQIKESLGAELRVTERRAEVPTAHPSPSPRPAGQFQTLV

VG
```

```
-continued
SEQ ID NO: 7 - PD-1 polypeptide variant euPD-1
(nucleotide sequence)
TTTCTCGAATCACCGGACAGACCCTGGAATGCGCCCACATTCTCACCAG

CACTTTTGCTGGTAGCAGAGGGCGATAATGCTACATTCACGTGTTCCTT

CAGTAATGCAAGCGAGTCATTTCATGTGGTTTGGCATCGAGAGTCACCT

AGTGGGCAGACTGATACACTTGCCGCATTCCCGGAAGATCGCTCCCAGC

CAGGTCAGGATCACCGGTTCAGGGTAACCCGACTGCCGAATGGGCGCGA

TTTCCATATGAGCGTTGTCCGGGCGCAACGGAACGATAGTGGAACATAC

GTGTGTGGCGTAATATCCCTCGCTCCCAAAATACAAATAAAGGAGTCTC

TGAGAGCAGAGCTGAGAGTGACAGAACGACGGGCGGAAGTTCCCACGGC

TCATCCGTCACCAAGTCCGCGCCCCGCAGGCCAATTTCAAACGCTCGTC

GTAGGC

SEQ ID NO: 8 - PD-1 polypeptide variant euPD-1
(amino acid)
FLESPDRPWNAPTFSPALLLVAEGDNATFTCSFSNASESFHVVWHRESP

SGQTDTLAAFPEDRSQPGQDHRFRVTRLPNGRDFHMSVVRAQRNDSGTY

VCGVISLAPKIQIKESLRAELRVTERRAEVPTAHPSPSPRPAGQFQTLV

VG
```

In all embodiment described herein the PD-1 variant may include additional residues at the C-terminus arising from selection of the restriction endonuclease used for cloning. It is preferred that the additional residues arising from cloning selection is limited to one, two, three, or four residues with preference given to a dipeptide addition, preferably an alanine-serine dipeptide. For example when used as the PD-1 polypeptide variant on its own or as part of a fusion construct, in the case of euPD-1, included in the present invention is the sequence of SEQ ID NO: 8 plus a C-terminal AS dipeptide. Such a sequence is envisioned and embraced by the defined level of amino acid sequence identity for the PD-1 polypeptide variant of the present invention.

In some embodiments, the PD-1 polypeptide variant of the present invention includes a PD-1 variant comprising an amino acid sequence having 95% or more (e.g., 96% or more, 97% or more, 98% or more, or 99% or more) sequence identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139. Included in the present invention is nucleic acid encoding a PD-1 polypeptide variant of this embodiment, a vector comprising the nucleic acid, a pharmaceutical composition comprising the PD-1 polypeptide variant of this embodiment, and a method of treating disease or condition (e.g., cancer) in a subject in need thereof by administering the pharmaceutical composition.

In a variant of this embodiment, the PD-1 polypeptide variant of the present invention includes a PD-1 variant comprising an amino acid sequence having 95% or more (e.g., 96% or more, 97% or more, 98% or more, or 99% or more) sequence identity to residues 24 to 172 of SEQ ID NO: 11, wherein said variant has a mutation at D26, P34, V43, T45, T59, V64, L65, N66, Y68, M70, N74, K78, Q99, L122, A125, A132, and R139. Included in the present invention is nucleic acid encoding a PD-1 polypeptide variant of this embodiment, a vector comprising the nucleic acid, a pharmaceutical composition comprising the PD-1 polypeptide variant of this embodiment, and a method of treating disease or condition (e.g., cancer) in a subject in need thereof by administering the pharmaceutical composition.

treating disease or condition (e.g., cancer) in a subject in need thereof by administering the pharmaceutical composition.

In some embodiments, the PD-1 polypeptide variant of the present invention includes a PD-1 variant comprising an amino acid sequence having 95% or more (e.g., 96% or more, 97% or more, 98% or more, or 99% or more) sequence identity to residues 24 to 172 of SEQ ID NO: 11, wherein said variant has a mutation at D26, P34, V43, T45, T59, V64, L65, N66, Y68, M70, N74, K78, C93, Q99, R114, L122, A125, A132, and R139. Included in the present invention is nucleic acid encoding a PD-1 polypeptide variant of this embodiment, a vector comprising the nucleic acid, a pharmaceutical composition comprising the PD-1 polypeptide variant of this embodiment, and a method of treating disease or condition (e.g., cancer) in a subject in need thereof by administering the pharmaceutical composition.

Preferred mutations include: D26E, P34A, V43L, T45A, T59A, V64H, L65V, N66V, Y68H, M70E, N74G, K78T, C93H, Q99R, R114Q, L122V, A125V, A132I, R139G.

Fc-Fusion Proteins and Encoding Nucleotide Sequence

As used herein, "Fc-fusion proteins" refer to engineered proteins composed of the Fc domain of IgG linked to a polypeptide or protein of interest. Examples of Fc-fused polypeptides or proteins include, but are not limited to, single peptides, ligands activated upon cell-surface receptor binding, signaling molecules (e.g., cytokines), extracellular domains of a receptor activated upon dimerization, and bait proteins used to identify binding partners in protein microarrays. In some embodiments, a Fc-fusion protein acts as an antibody agent that specifically binds to a particular antigen via an antigen binding domain. In some embodiments, the Fc fusion protein includes a polypeptide or polypeptide complex that includes immunoglobulin structural elements sufficient to confer specific binding.

Fc is the constant domain selected from an IgG1 or a variant thereof, an IgG2 or a variant thereof, an IgG4 or a variant thereof, as well as humanized IgG1/2 or a variant thereof. Fc plays multiple roles in dimerization for formation of Y-shaped structure of Ig and maintenance of the structure, and Fc-mediated effector functions and extension of serum half-life. In some embodiments, there are two domains, second constant domain (CH2) and third constant domain (CH3) in monomeric Fc. In some embodiments, the fusion protein includes a linker that fuses the Fc domain and specific peptide or protein together. In some embodiments, the immunoglobulin Fc region is linked to the specific peptide or protein by a peptide bond. In some embodiments, the immunoglobulin Fc region is linked to the specific peptide or protein by a peptide linker sequence. In some embodiments, the linker sequence comprises a $(G_4S)_2$(SEQ ID NO: 19), a $(G_4S)_3$ linker (SEQ ID NO: 20), or a 218 linker (SEQ ID NO: 21).

In some embodiments, the specific peptide or protein is linked to the carboxy-terminus of the immunoglobulin Fc region. In some embodiments, the Fc domain comprises SEQ ID NO: 10 or SEQ ID NO: 16 or a sequence having 95% or more (e.g., 96% or more, 97% or more, 98% or more, or 99% or more) sequence identity to SEQ ID NO: 10 or SEQ ID NO: 16.

In some embodiments, a PD-1 polypeptide variant is used to produce a PD-1 fusion protein. In some embodiments, a PD-1 fusion protein can include a PD-1 polypeptide variant and an immunoglobulin Fc region. In some embodiments, a PD-1 Fc fusion protein comprises an immunoglobulin Fc region, and a PD-1 polypeptide variant linked by a peptide bond or a peptide linker sequence to the carboxy-terminus of the immunoglobulin Fc region, wherein the PD-1 polypeptide variant comprises an amino acid sequence having 95% or more (e.g., 96% or more, 97% or more, 98% or more, 99% or more) sequence identity to SEQ ID NO: 4, SEQ ID NO: 6, or SEQ ID NO: 8.

In some embodiments, the immunoglobulin Fc region comprises an amino acid sequence having 95% or more (e.g., 96% or more, 97% or more, 98% or more, or 99% or more) sequence identity to SEQ ID NO: 10 or SEQ ID NO: 16.

In some embodiments, a PD-1 Fc fusion protein has increased binding affinity to a PD-L1 molecule as compared to a wild-type PD-1 polypeptide. In some embodiments, a PD-1 Fc fusion protein has a binding affinity ($K_D$) for a PD-L1 molecule of about $1\times10^{-8}$ to $1\times10^{-10}$ M, preferably of about $1\times10^{-9}$ to $1\times10^{-10}$ M. In some embodiments, a PD-1 Fc fusion protein has a binding affinity (KD) for a PD-L1 molecule of about $1.10\times10^{-9}$ M, about $1.037\times10^{-9}$ M, or about $7.14\times10^{-10}$ M.

As used herein, "nucleic acid" is used to include any compound and/or substance that comprise polynucleotides. Exemplary nucleic acids or polynucleotides can include, but are not limited to, ribonucleic acids (RNAs) and/or deoxyribonucleic acids (DNAs).

In some embodiments, nucleic acid constructs include regions that encode an immunoglobulin Fc region and a PD-1 polypeptide variant. In some embodiments, the sequence encoding the Fc domain comprises nucleotide sequence having 95% or more (e.g., 95% or more, 96% or more, 97% or more, 98% or more, or 99% or more) sequence identity to SEQ ID NO: 9.

```
SEQ ID NO: 9 - Fc (207-230 IMGT allele IGHG1*03,
231- 457 IMGT allele IGHG2*01)
AGCAACACTAAAGTCGACAAGCGAGTAGAACCGAAATCATGCGACAAAA

CACATACGTGCCCTCCCTGCCCAGCACCACCTGTCGCGGGCCCCTCTGT

TTTCCTGTTTCCACCCAAGCCAAAGGACACATTGATGATTTCCCGGACT

CCTGAAGTCACCTGCGTGGTAGTAGATGTATCACATGAAGATCCAGAAG

TCCAGTTCAACTGGTATGTGGACGGAGTAGAGGTACATAATGCCAAGAC

CAAACCACGGGAAGAGCAGTTCAACAGTACTTTCCGGGTAGTTAGCGTT

TTGACTGTCGTACACCAAGACTGGCTTAATGGAAAAGAATACAAGTGTA

AGGTAAGCAACAAGGGCCTGCCGGCTCCGATAGAGAAACCATTAGCAA

GACAAAGGGCCAACCACGCGAACCCCAGGTATATACCCTCCCACCGTCC

CGCGAGGAGATGACTAAGAATCAAGTTTCTCTCACGTGCTTGGTAAAGG

GCTTCTATCCGAGCGATATAGCCGTGGAGTGGGAGTCTAATGGTCAGCC

CGAAAACAATTACAAAACTACGCCTCCTATGCTGGACAGTGATGGGAGC

TTCTTTCTTTACAGTAAGCTTACCGTGGACAAGTCTCGGTGGCAACAAG

GAAATGTTTTTAGTTGTTCTGTAATGCATGAAGCACTTCATAACCATTA

CACCCAGAAAGTCTGAGCTTGTCCCCGGGAAAA

SEQ ID NO: 10 - Fc (207-230 IMGT allele IGHG1*03,
231- 457 IMGT allele IGHG2*01) (amino acid)
SNTKVDKRVEPKSCDKTHTCPPCPAPPVAGPSVFLFPPKPKDTLMISRT

PEVTCVVVDVSHEDPEVQFNWYVDGVEVHNAKTKPREEQFNSTFRVVSV

LTVVHQDWLNGKEYKCKVSNKGLPAPIEKTISKTKGQPREPQVYTLPPS
```

```
                        -continued
REEMTKNQVSLTCLVKGFYPSDIAVEWESNGQPENNYKTTPPMLDSDGS

FFLYSKLTVDKSRWQQGNVFSCSVMHEALHNHYTQKSLSLSPGK
```

As explained above, in all embodiment described herein the PD-1 variant may include additional residues at the C-terminus arising from selection of the restriction endonuclease used for cloning. It is preferred that the additional residues arising from cloning selection is limited to one, two, three, or four residues with preference given to a dipeptide addition, preferably an alanine-serine dipeptide. For example when used as the PD-1 polypeptide variant on its own or as part of a fusion construct, in the case of euPD-1, included in the present invention is the sequence of SEQ ID NO: 8 plus a C-terminal AS dipeptide. Such a sequence is envisioned and embraced by the defined level of amino acid sequence identity for the PD-1 polypeptide variant of the present invention. Thus, in a fusion construct of this embodiment the residues arising from cloning may be located before the linker.

Also embraced by the present invention is a PD-1 Fc fusion protein wherein multiple copies of the PD-1 polypeptide variant is present, each separated by a linker. The term "multiple copies of the PD-1 polypeptide variant" means that two, three, or four PD-1 polypeptide variants may be present wherein the variants present may be the same or different. In addition, the linker separating the respective PD-1 polypeptide variants may be the same or different. Also, the linker between the PD-1 polypeptide variants may be different from the linker between the PD-1 polypeptide variant and the polypeptide or protein of interest.

In some embodiments, the PD-1 polypeptide variant for the PD-1 Fc fusion protein comprises an amino acid sequence having 95% or more (e.g., 96% or more, 97% or more, 98% or more, or 99% or more) sequence identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139. Included in the present invention is nucleic acid encoding a PD-1 polypeptide variant of this embodiment, a vector comprising the nucleic acid, a pharmaceutical composition comprising the PD-1 polypeptide variant of this embodiment, and a method of treating disease or condition (e.g., cancer) in a subject in need thereof by administering the pharmaceutical composition.

In a variant of this embodiment, the PD-1 polypeptide variant for the PD-1 Fc fusion protein comprises an amino acid sequence having 95% or more (e.g., 96% or more, 97% or more, 98% or more, or 99% or more) sequence identity to residues 24 to 172 of SEQ ID NO: 11, wherein said variant has a mutation at D26, P34, V43, T45, T59, V64, L65, N66, Y68, M70, N74, K78, Q99, L122, A125, A132, and R139. Included in the present invention is nucleic acid encoding a PD-1 polypeptide variant of this embodiment, a vector comprising the nucleic acid, a pharmaceutical composition comprising the PD-1 polypeptide variant of this embodiment, and a method of treating disease or condition (e.g., cancer) in a subject in need thereof by administering the pharmaceutical composition.

In some embodiments, the PD-1 polypeptide variant for the PD-1 Fc fusion protein comprises an amino acid sequence having 95% or more (e.g., 96% or more, 97% or more, 98% or more, or 99% or more) sequence identity to residues 24 to 172 of SEQ ID NO: 11, wherein said variant has a mutation at D26, P34, V43, T45, T59, V64, L65, N66, Y68, M70, N74, K78, C93, Q99, R114, L122, A125, A132, and R139. Included in the present invention is nucleic acid encoding a PD-1 polypeptide variant of this embodiment, a vector comprising the nucleic acid, a pharmaceutical composition comprising the PD-1 polypeptide variant of this embodiment, and a method of treating disease or condition (e.g., cancer) in a subject in need thereof by administering the pharmaceutical composition.

Preferred mutations include: D26E, P34A, V43L, T45A, T59A, V64H, L65V, N66V, Y68H, M70E, N74G, K78T, C93H, Q99R, R114Q, L122V, A125V, A132I, R139G.

As stated above, in some embodiments, the immunoglobulin Fc region comprises an amino acid sequence having 95% or more (e.g., 96% or more, 97% or more, 98% or more, or 99% or more) sequence identity to SEQ ID NO: 10 or SEQ ID NO: 16.

4-1BB 4-1BB (also referred to as CD137, TNFRSF9) is a receptor belonging to the tumor necrosis factor receptor (TNFR) superfamily. 4-1BB is a co-stimulatory molecule generally expressed in activated T lymphocytes and involved in immunity and autoimmune diseases (Kwon et al. PNAS 84: 2896, 1987; Kwon et al. PNAS 86: 1963, 1989; Son et al. Journal of Immunological Methods 286 (1-2): 187-201, 2004, each of which is herein incorporated by reference in its entirety). Human 4-1BB is a 255 amino acid protein and expressed on the cell surface in monomer (30 kDa) and dimer (55 kDa) forms and likely trimerizes with 4-1BB ligand to signal.

Further, 4-1BB is constitutively expressed on a number of cells, albeit at low levels, including Foxp3$^+$ Tregs and dendritic cells (DC). Activation with a number of agonists, such as cytokines (e.g., IL-2, IL-4), polyclonal activators (e.g., Con A and PHA), cell surface molecules (e.g., anti-CD3, anti-CD28) and promoters of Ca$^{2+}$ induction and PKC activity (e.g., ionomycin, photbol myristate acetate) further enhance expression of 4-1BB.

Numerous studies of murine and human T cells indicate that 4-1BB promotes enhanced cellular proliferation, survival, and cytokine production. Studies have indicated that some 4-1BB agonist monoclonal antibodies can increase costimulatory molecule expression and markedly enhance cytolytic T lymphocyte responses, resulting in anti-tumor efficacy in prophylactic and therapeutic settings. Further, 4-1BB monotherapy and combination therapy tumor models have established durable anti-tumor protective T cell memory responses. 4-1BB agonists also have been shown to inhibit autoimmune reactions in a variety of art-recognized autoimmunity models. This dual activity of 4-1BB offers the potential to provide anti-tumor activity while dampening autoimmune side effects that can be associated with immunotherapy approaches.

In some embodiments herein, the fusion protein may contain as the immunoglobulin Fc region an anti-4-1BB antibody domain. Specifically, an anti-4-1BB antibody domain can be produced using 94kvt clones (WO2018-127787, incorporated herein by reference in its entirety) possessing an anti-4-1BB antibody domain (94kvt) as a single chain Fv (scFv). Examples of suitable scFvs for the anti-4-1BB antibody, VH-218 linker-VL (HLC 218) and VL-218 linker-VH (LHC 218). The 94kvt VH sequence is shown in SEQ ID NO: 17, while the 94kvt VL sequence is shown in SEQ NO: 18 and the 218 liker is shown in SEQ ID NO: 21. Further, the scFv variant 94kvt HLC 218 is shown in SEQ ID NO: 22 and the scFv variant 94kvt LHC 218 is shown in SEQ ID NO: 23.

In some embodiments, the anti-4-1BB antibody domain (94kvt) as a single chain Fv (scFv) includes a sequence that is at least 70% identical (e.g., at least 75% identical, at least 80% identical, at least 85% identical, at least 90% identical, at least 95% identical, at least 96% identical, at least 97% identical, at least 98% identical, at least 99% identical, or 100% identical) to SEQ ID NO: 22 or SEQ ID NO: 23.

Thus, in an embodiment of the present invention is a Fc fusion BsAb (Bispecific antibody) comprising; an immunoglobulin Fc region; and a PD-1 polypeptide variant linked by a peptide bond or a peptide linker sequence to the N-terminus of the immunoglobulin Fc region, wherein the PD-1 polypeptide variant comprises an amino acid sequence having 95% or more (e.g., 96% or more, 97% or more, 98% or more, 99% or more) sequence identity to SEQ ID NO: 4, SEQ ID NO: 6, or SEQ ID NO: 8; and a scFv for the anti-4-1BB antibody linked by a peptide bond or a peptide linker sequence to the C— terminus of the immunoglobulin Fc region, wherein the scFv for the anti-4-1BB antibody comprises an amino acid sequence having 95% or more (e.g., 96% or more, 97% or more, 98% or more, 99% or more) sequence identity to an amino acid sequence comprising SEQ ID NO: 17 and 18 linked by a peptide bond or a peptide linker sequence.

Also provided is a Fc fusion BsAb (Bispecific antibody) comprising; an immunoglobulin Fc region; and a PD-1 polypeptide variant linked by a peptide bond or a peptide linker sequence to the N-terminus of the immunoglobulin Fc region, wherein the PD-1 polypeptide variant comprises an amino acid sequence having 95% or more (e.g., 96% or more, 97% or more, 98% or more, 99% or more) sequence identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139; and a scFv for the anti-4-1BB antibody linked by a peptide bond or a peptide linker sequence to the C— terminus of the immunoglobulin Fc region, wherein the scFv for the anti-4-1BB antibody comprises an amino acid sequence having 95% or more (e.g., 96% or more, 97% or more, 98% or more, 99% or more) sequence identity to an amino acid sequence comprising SEQ ID NO: 17 and 18 linked by a peptide bond or a peptide linker sequence.

In some embodiments, the immunoglobulin Fc region comprises an amino acid sequence having 95% or more (e.g., 96% or more, 97% or more, 98% or more, or 99% or more) sequence identity to SEQ ID NO: 10 or SEQ ID NO: 16.

In some embodiments the scFv for the anti-4-1BB antibody is an amino acid sequence that is at least 70% identical (e.g., at least 75% identical, at least 80% identical, at least 85% identical, at least 90% identical, at least 95% identical, at least 96% identical, at least 97% identical, at least 98% identical, at least 99% identical, or 100% identical) to SEQ ID NO: 22 or SEQ ID NO: 23.

Examples of the linker sequence include a $(G_4S)_2$(SEQ ID NO: 19), a $(G_4S)_3$ linker (SEQ ID NO: 20), or a 218 linker (SEQ ID NO: 21).

The bispecific antibody described herein has increased binding affinity to a PD-L1 molecule as compared to a wild-type PD-1 polypeptide and specific binding affinity to 4-1BB.

The BsAb antibody of the present invention has decreased or no antibody-dependent cellular cytotoxicity (ADCC) and/or complement-dependent cytotoxicity (CDC) effects.

The BsAb antibody of the present invention demonstrates decreased or no hepatotoxicity.

Vectors

In some embodiments, nucleic acid constructs described above may be inserted into an expression vector or viral vector by methods known to the art, and nucleic acid molecules may be operably linked to an expression control sequence. Non-limiting examples of expression vectors include plasmid vectors, transposon vectors, cosmid vectors, and viral derived vectors (e.g., any adenoviral derived vectors (AV), cytomegaloviral derived (CMV) vectors, simian viral derived (SV40) vectors, adeno-associated virus (AAV) vectors, lentivirus vectors, and retroviral vectors). In some embodiments, the expression vector is a viral vector.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art.

In some embodiments, nucleic acid molecules are inserted into a vector that is able to express a PD-1 polypeptide variant of the present disclosure or a PD-1 Fc fusion protein when introduced into an appropriate cell.

Therapeutic Applications

In some embodiments, the PD-1 polypeptide variants, PD-1 Fc fusion proteins, or nucleic acid constructs described herein may be used for treating a subject in need thereof. In some embodiments, the subject is diagnosed with a PD-L1 associated disease. In some embodiments, the subject is diagnosed with a PD-L1 associated cancer. In some embodiments, a pharmaceutical composition that includes a PD-1 polypeptide variant or a PD-1 Fc fusion protein, and a pharmaceutically acceptable carrier can be administered to the subject diagnosed with a PD-L1 associated disease. In some embodiments, the pharmaceutical composition can be administered with one or more additional anticancer therapies that include, but are not limited to, ionizing radiation, a chemotherapeutic agent, a therapeutic antibody, and a checkpoint inhibitor.

The PD-1/PD-L1 pathway represents an adaptive immune resistance mechanism used by tumor cells in response to endogenous immune anti-tumor activity. PD-L1 expressed on tumor cells binds to PD-1 receptors on activated T cells, which leads to the inhibition of the cytotoxic T cells. In some embodiments, PD-1 polypeptide variants are used as PD-L1 inhibitors to treat cancers that can include, but are not limited to, non-small cell lung cancer, lung adenocarcinoma, gastric cancer, and breast cancer.

Cancer can refer to a broad group of diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. Cancer or cancer tissue may include a tumor.

Cancers suitable for treatment by a method of the present disclosure can include, but are not limited to, bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, and prostate cancer. In some embodiments, a cancer for treatment by a method of the present disclosure can include may include, but is not limited to, carcinoma, lymphoma (e.g., Hodgkin's and non-Hodgkin's lymphomas), blastoma, sarcoma, and leukemia. In some embodiments, cancer may include squamous cell carcinoma, small cell lung cancer, non-small cell lung cancer, lung adenocarcinoma, squamous cell carcinoma of the lung, peritoneal cancer, hepatocellular carcinoma, gastric cancer, pancreatic cancer, glioma, cervical cancer, ovarian cancer, liver cancer, bladder cancer, hepatocellular carcinoma, breast cancer, colon cancer, colorectal cancer, endometrial or uterine carcinoma, salivary carcinoma, kidney cancer, prostate cancer, vulvar cancer, thyroid cancer, liver carcinoma, leukemia and other lymphoproliferative disorders, and various types of head and neck cancer.

In some embodiments, the cancer can be an embryonal tumor (Wilms tumor, hepatoblastoma, rhabdoid, neuroblastoma), germ cell tumor (yolk sac tumor, immature teratoma, and embryonal carcinoma), carcinoma (hepatocellular carcinoma and pulmonary squamous cell carcinoma), sarcoma (malignant rhabdoid tumor and RMS), or malignant melanoma.

The fusion proteins and bispecific antibody of the present invention have the increased advantage that they have decreased or no antibody-dependent cellular cytotoxicity (ADCC) and/or complement-dependent cytotoxicity (CDC) effects. Further, fusion proteins and bispecific antibody of the present invention have decreased or no hepatotoxicity.

In the context of the present description, all publications, patent applications, patents and other references mentioned herein, if not otherwise indicated, are explicitly incorporated by reference herein in their entirety for all purposes as if fully set forth, and shall be considered part of the present disclosure in their entirety.

Unless otherwise defined, all technical and scientific terms used herein have the same meaning as commonly understood by one of ordinary skill in the art to which this disclosure belongs. In case of conflict, the present specification, including definitions, will control.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Without being bound to the following specific embodiments, the present invention is exemplified by the follow:

(1) A programmed cell death 1 (PD-1) polypeptide variant comprising an amino acid sequence having 95% or more (e.g., 96% or more, 97% or more, 98% or more, or 99% or more) sequence identity to SEQ ID NO: 4, SEQ ID NO: 6, or SEQ ID NO: 8, wherein the PD-1 polypeptide variant comprises:

an extracellular domain that binds specifically to programmed cell death 1 ligand (PD-L1); and a transmembrane domain or a fragment thereof.

(2) The PD-1 polypeptide variant of (1), wherein the PD-1 polypeptide variant comprises an amino acid sequence having 97% or more sequence identity to SEQ ID NO: 4, SEQ ID NO: 6, or SEQ ID NO: 8.

(3) The PD-1 polypeptide variant of any one of (1) or (2), wherein the PD-1 polypeptide variant comprises an amino acid sequence having 98% or more sequence identity to SEQ ID NO: 4, SEQ ID NO: 6, or SEQ ID NO: 8.

(4) The PD-1 polypeptide variant any one of (1) to (3), wherein the PD-1 polypeptide variant comprises an amino acid sequence of SEQ ID NO: 4, SEQ ID NO: 6, or SEQ ID NO: 8.

(5) The PD-1 polypeptide variant of (1), wherein the PD-1 polypeptide variant comprises SEQ ID NO: 4.

(6) The PD-1 polypeptide variant of (1), wherein the PD-1 polypeptide variant comprises SEQ ID NO: 6.

(7) The PD-1 polypeptide variant of (1), wherein the PD-1 polypeptide variant comprises SEQ ID NO: 8.

(8) The PD-1 polypeptide variant of any one of (1) to (7), wherein the transmembrane domain comprises at least two amino acid residues.

(9) The PD-1 polypeptide variant of any one of (1) to (8), wherein the transmembrane domain comprises at least 5 amino acid residues.

(10) The PD-1 polypeptide variant of any one of (1) to (9), wherein the transmembrane domain comprises at least 10 amino acid residues.

(11) The PD-1 polypeptide variant of any one of (1) to (10), wherein the polypeptide variant has increased binding affinity to a PD-L1 molecule as compared to a wild-type PD-1 polypeptide.

(12) The PD-1 polypeptide variant of any one of (1) to (11), wherein the polypeptide variant has a binding affinity (KD) for a PD-L1 molecule of about $1 \times 10^{-8}$ to $1 \times 10^{-10}$ M.

(13) The PD-1 polypeptide variant of any one of (1) to (12), wherein the polypeptide variant has a binding affinity (KD) for a PD-L1 molecule of about $1.10 \times 10^{-9}$ M, about $1.037 \times 10^{-9}$ M, or about $7.14 \times 10^{-10}$ M.

(14) A PD-1 Fc fusion protein comprising:

an immunoglobulin Fc region; and a PD-1 polypeptide variant linked by a peptide bond or a peptide linker sequence to the carboxy-terminus of the immunoglobulin Fc region, wherein the PD-1 polypeptide variant comprises an amino acid sequence having 95% or more (e.g., 96% or more, 97% or more, 98% or more, or 99% or more) sequence identity to SEQ ID NO: 4, SEQ ID NO: 6, or SEQ ID NO: 8.

(15) The PD-1 Fc fusion protein of (14), wherein the immunoglobulin Fc region comprises an amino acid sequence having 95% or more (e.g., 96% or more, 97% or more, 98% or more, or 99% or more) sequence identity to SEQ ID NO: 10 or SEQ ID NO: 16.

(16) The PD-1 Fc fusion protein of any one of (14) to (15), wherein the fusion protein has increased binding affinity to a PD-L1 molecule as compared to a wild-type PD-1 polypeptide.

(17) The PD-1 Fc fusion protein of any one of (14) to (16), wherein the fusion protein has a binding affinity (KD) for a PD-L1 molecule of about $1 \times 10^{-8}$ to $1 \times 10^{-10}$ M.

(18) The PD-1 Fc fusion protein of any one of (14) to (17), wherein the fusion protein has a binding affinity (KD)

for a PD-L1 molecule of about $1.10 \times 10^{-9}$ M, about $1.037 \times 10^{-9}$ M, or about $7.14 \times 10^{-10}$ M.

(19) The PD-1 Fc fusion protein of any one of (14) to (18), wherein the PD-1 polypeptide variant is linked by a peptide linker sequence to the carboxy-terminus of the immunoglobulin Fc region.

(20) The PD-1 Fc fusion protein of any one of (14) to (19), wherein the peptide linker sequence is selected from the group consisting of SEQ ID NO: 19, SEQ ID NO: 20, and SEQ ID NO: 21.

(21) The PD-1 Fc fusion protein of any one of (14) to (20), wherein the more than one copy of the PD-1 polypeptide variant is present wherein the copies may be the same or different and are linked by a peptide linker sequence.

(22) The PD-1 Fc fusion protein of (21), wherein two copies of PD-1 polypeptide variant is present.

(23) The PD-1 Fc fusion protein of any one of (21) or (22), wherein the peptide linker sequence is selected from the group consisting of SEQ ID NO: 19, SEQ ID NO: 20, and SEQ ID NO: 21.

(24) The PD-1 Fc fusion protein of any one of (14) to (23), wherein the PD-1 Fc fusion protein is selected from the group consisting of SEQ ID NO: 12, SEQ ID NO: 13, SEQ ID NO; 14, and SEQ ID NO: 15.

(25) A nucleic acid comprising:

a sequence encoding a PD-1 polypeptide variant, wherein the polypeptide variant comprises a sequence having 95% or more (e.g., 96% or more, 97% or more, 98% or more, or 99% or more) sequence identity to SEQ ID NO: 3, SEQ ID NO: 5, or SEQ ID NO: 7.

(26) The nucleic acid of (25), further comprising:

a sequence encoding an immunoglobulin Fc region, wherein the sequence encoding the immunoglobulin Fc region comprises SEQ ID NO: 9.

(27) An expression vector comprising the nucleic acid of any one of (25) or (26).

(28) The vector of (27), wherein the vector is a viral vector.

(29) A pharmaceutical composition comprising:

the PD-1 polypeptide variant of any one of (1) to (13) or the PD-1 fusion protein of any one of (14) to (24); and a pharmaceutically acceptable carrier.

(30) A method of treating a disease or a condition in a subject in need thereof, the method comprising:

administering to the subject the pharmaceutical composition of (29), thereby treating a disease or a condition.

(31) The method of (30), wherein the subject has cancer.

(32) The method of (31), wherein the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

(33) The method of any of (30) to (32), wherein when the pharmaceutical composition comprises the PD-1 fusion protein of any one of (14) to (24), decreased or no antibody-dependent cellular cytotoxicity (ADCC) and/or complement-dependent cytotoxicity (CDC) effects are observed.

(34) The method of any of (30) to (33), wherein when the pharmaceutical composition comprises the PD-1 fusion protein of any one of (14) to (24), decreased or no hepatotoxicity is observed.

(35) A programmed cell death 1 (PD-1) polypeptide variant comprising an amino acid sequence having 95% or more (e.g., 96% or more, 97% or more, 98% or more, or 99% or more) sequence identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139.

(36) The PD-1 polypeptide variant of (35), wherein said variant comprises a mutation at D26, P34, V43, T45, T59, V64, L65, N66, Y68, M70, N74, K78, Q99, L122, A125, A132, and R139.

(37) The PD-1 polypeptide variant of (35), wherein said variant comprises a mutation at D26, P34, V43, T45, T59, V64, L65, N66, Y68, M70, N74, K78, C93, Q99, R114, L122, A125, A132, and R139.

(38) The PD-1 polypeptide variant of any one of (35) to (37), wherein said mutations are D26E, P34A, V43L, T45A, T59A, V64H, L65V, N66V, Y68H, M70E, N74G, K78T, C93H, Q99R, R114Q, L122V, A125V, A132I, or R139G.

(39) The PD-1 polypeptide variant of any one of (35) to (38), wherein the PD-1 polypeptide variant comprises an amino acid sequence having 97% or more sequence identity to identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139.

(40) The PD-1 polypeptide variant of any one of (35) to (39), wherein the PD-1 polypeptide variant comprises an amino acid sequence having 98% or more sequence identity to identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139.

(41) The PD-1 polypeptide variant of any one of (35) to (40), wherein the polypeptide variant has increased binding affinity to a PD-L1 molecule as compared to a wild-type PD-1 polypeptide.

(42) The PD-1 polypeptide variant of any one of (35) to (41), wherein the polypeptide variant has a binding affinity (KD) for a PD-L1 molecule of about $1 \times 10^{-8}$ to $1 \times 10^{-10}$ M.

(43) A PD-1 Fc fusion protein comprising:
an immunoglobulin Fc region; and
a PD-1 polypeptide variant of any one of (35) to (42) linked by a peptide bond or a peptide linker sequence to the carboxy-terminus of the immunoglobulin Fc region.

(44) The PD-1 Fc fusion protein of (43), wherein the immunoglobulin Fc region comprises an amino acid sequence having 95% or more (e.g., 96% or more, 97% or more, 98% or more, or 99% or more) sequence identity to SEQ ID NO: 10 or SEQ ID NO: 16.

(45) The PD-1 Fc fusion protein of any one of (43) or (44), wherein the fusion protein has increased binding affinity to a PD-L1 molecule as compared to a wild-type PD-1 polypeptide.

(46) The PD-1 Fc fusion protein of any one of (43) to (45) wherein the fusion protein has a binding affinity (KD) for a PD-L1 molecule of about $1 \times 10^{-8}$ to $1 \times 10^{-10}$ M.

(47) The PD-1 Fc fusion protein of any one of (43) to (46), wherein the PD-1 polypeptide variant is linked by a peptide linker sequence to the carboxy-terminus of the immunoglobulin Fc region.

(48) The PD-1 Fc fusion protein of any one of (43) to (47), wherein the peptide linker sequence is selected from the group consisting of SEQ ID NO: 19, SEQ ID NO: 20, and SEQ ID NO: 21.

(49) The PD-1 Fc fusion protein of any one of (43) to (48), wherein the more than one copy of the PD-1 polypeptide variant is present wherein the copies may be the same or different and are linked by a peptide linker sequence.

(50) The PD-1 Fc fusion protein of (49), wherein two copies of PD-1 polypeptide variant is present.

(51) The PD-1 Fc fusion protein of any one of (49) or (50), wherein the peptide linker sequence is selected from the group consisting of SEQ ID NO: 19, SEQ ID NO: 20, and SEQ ID NO: 21.

(52) A nucleic acid comprising:
a sequence encoding a PD-1 polypeptide variant of any one of (35) to (51).

(53) The nucleic acid of (52), further comprising:
a sequence encoding an immunoglobulin Fc region.

(54) An expression vector comprising the nucleic acid of any one of (52) or (53).

(55) The vector of (54), wherein the vector is a viral vector.

(56) A pharmaceutical composition comprising:
the PD-1 polypeptide variant of any one of (35) to (42) or the PD-1 fusion protein of any one of (43) to (51); and
a pharmaceutically acceptable carrier.

(57) A method of treating a disease or a condition in a subject in need thereof, the method comprising:
administering to the subject the pharmaceutical composition of (56), thereby treating a disease or a condition.

(58) The method of (57), wherein the subject has cancer.

(59) The method of (58), wherein the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

(60) The method of any of (57) to (59), wherein when the pharmaceutical composition comprises the PD-1 fusion protein of any one of (43) to (51), decreased or no antibody-dependent cellular cytotoxicity (ADCC) and/or complement-dependent cytotoxicity (CDC) effects are observed.

(61) The method of any of (57) to (60), wherein when the pharmaceutical composition comprises the PD-1 fusion protein of any one of (43) to (51), decreased or no hepatotoxicity is observed.

(62) A bispecific antibody comprising:
an immunoglobulin Fc region;
a PD-1 polypeptide variant linked by a peptide bond or a peptide linker sequence to the N-terminus of the immunoglobulin Fc region, wherein the PD-1 polypeptide variant comprises an amino acid sequence having 95% or more (e.g., 96% or more, 97% or more, 98% or more, or 99% or more) sequence identity to SEQ ID NO: 4, SEQ ID NO: 6, or SEQ ID NO: 8; and a scFv for the anti-4-1BB antibody linked by a peptide bond or a peptide linker sequence to the C-terminus of the immunoglobulin Fc region, wherein the scFv for the anti-4-1BB antibody comprises an amino acid sequence having 95% or more (e.g., 96% or more, 97% or more, 98% or more, or 99% or more) sequence identity to an amino acid sequence comprising SEQ ID NO: 17 and 18 linked by a peptide bond or a peptide linker sequence.

(63) The bispecific antibody of (62), wherein the immunoglobulin Fc region comprises an amino acid sequence having 95% or more (e.g., 96% or more, 97% or more, 98% or more, or 99% or more) sequence identity to SEQ ID NO: 10 or SEQ ID NO: 16.

(64) The bispecific antibody of any of (62) or (63), wherein the PD-1 polypeptide variant is linked by a peptide linker sequence to the N-terminus of the immunoglobulin Fc region.

(65) The bispecific antibody of any of (62) to (64), wherein the scFv for the anti-4-1BB antibody is linked by peptide linker sequence to the C-terminus of the immunoglobulin Fc region.

(66) The bispecific antibody of any of (62) to (65), wherein the peptide linker sequence is selected from the group consisting of SEQ ID NO: 19, SEQ ID NO: 20, and SEQ ID NO: 21.

(67) The bispecific antibody of any of (62) to (66), wherein the scFv for the anti-4-1BB antibody comprises SEQ ID NO: 22 or SEQ ID NO: 23 or a sequence that is at least 70% identical (e.g., at least 75% identical, at least 80% identical, at least 85% identical, at least 90% identical, at least 95% identical, at least 96% identical, at least 97% identical, at least 98% identical, at least 99% identical, or 100% identical) to SEQ ID NO: 22 or SEQ ID NO: 23.

(68) The bispecific antibody of any of (62) to (67), wherein the bispecific antibody has increased binding affinity to a PD-L1 molecule as compared to a wild-type PD-1 polypeptide and specific binding affinity to 4-1BB.

(69) A pharmaceutical composition comprising:

the bispecific antibody of any of (62) to (68); and a pharmaceutically acceptable carrier.

(70) A method of treating a disease or a condition in a subject in need thereof, the method comprising:

administering to the subject the pharmaceutical composition of (69), thereby treating a disease or a condition.

(71) The method of (70), wherein the subject has cancer.

(72) The method of (71), wherein the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

(73) The method of any of (70) to (72), wherein decreased or no antibody-dependent cellular cytotoxicity (ADCC) and/or complement-dependent cytotoxicity (CDC) effects are observed.

(74) The method of any of (70) to (73), wherein decreased or no hepatotoxicity is observed.

(75) A bispecific antibody comprising:

an immunoglobulin Fc region;

a PD-1 polypeptide variant linked by a peptide bond or a peptide linker sequence to the N-terminus of the immunoglobulin Fc region, wherein the PD-1 polypeptide variant comprises an amino acid sequence having 95% or more (e.g., 96% or more, 97% or more, 98% or more, 99% or more) sequence identity to residues 24 to 172 of SEQ ID NO: 11, wherein said variant has a mutation at least at one residue selected from the group consisting of D26, P34, V43, T45, T59, V64, L65, N66, Y68, M70, N74, K78, C93, Q99, R114, L122, A125, A132, and R139; and a scFv for the anti-4-1BB antibody linked by a peptide bond or a peptide linker sequence to the C-terminus of the immunoglobulin Fc region, wherein the scFv for the anti-4-1BB antibody comprises an amino acid sequence having 95% or more (e.g., 96% or more, 97% or more, 98% or more, or 99% or more) sequence identity to an amino acid sequence comprising SEQ ID NO: 17 and 18 linked by a peptide bond or a peptide linker sequence.

(76) The bispecific antibody of (75), wherein the immunoglobulin Fc region comprises an amino acid sequence having 95% or more (e.g., 96% or more, 97% or more, 98% or more, or 99% or more) sequence identity to SEQ ID NO: 10 or SEQ ID NO: 16.

(77) The bispecific antibody of any of (75) or (76), wherein the PD-1 polypeptide variant is linked by a peptide linker sequence to the N-terminus of the immunoglobulin Fc region.

(78) The bispecific antibody of any of (75) to (77), wherein the scFv for the anti-4-1BB antibody is linked by peptide linker sequence to the C-terminus of the immunoglobulin Fe region.

(79) The bispecific antibody of any of (75) to (78), wherein the peptide linker sequence is selected from the group consisting of SEQ ID NO: 19, SEQ ID NO: 20, and SEQ ID NO: 21.

(80) The bispecific antibody of any of (75) to (79), wherein the scFv for the anti-4-1BB antibody comprises SEQ ID NO: 22 or SEQ ID NO: 23 or a sequence that is at least 70% identical (e.g., at least 75% identical, at least 80% identical, at least 85% identical, at least 90% identical, at least 95% identical, at least 96% identical, at least 97% identical, at least 98% identical, at least 99% identical, or 100% identical) to SEQ ID NO: 22 or SEQ ID NO: 23.

(81) The bispecific antibody of any of (75) to (80), wherein the bispecific antibody has increased binding affinity to a PD-L1 molecule as compared to a wild-type PD-1 polypeptide and specific binding affinity to 4-1BB.

(82) A pharmaceutical composition comprising:

the bispecific antibody of any of (75) to (81); and a pharmaceutically acceptable carrier.

(83) A method of treating a disease or a condition in a subject in need thereof, the method comprising:

administering to the subject the pharmaceutical composition of (82), thereby treating a disease or a condition.

(84) The method of (83), wherein the subject has cancer.

(85) The method of (84), wherein the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

(86) The method of any of (83) to (85), wherein decreased or no antibody-dependent cellular cytotoxicity (ADCC) and/or complement-dependent cytotoxicity (CDC) effects are observed.

(87) The method of any of (83) to (86), wherein decreased or no hepatotoxicity is observed.

EXAMPLES

The disclosure is further described in the following examples, which do not limit the scope of the disclosure described in the claims.

Example 1—Variants of PD-1

Figure 2:
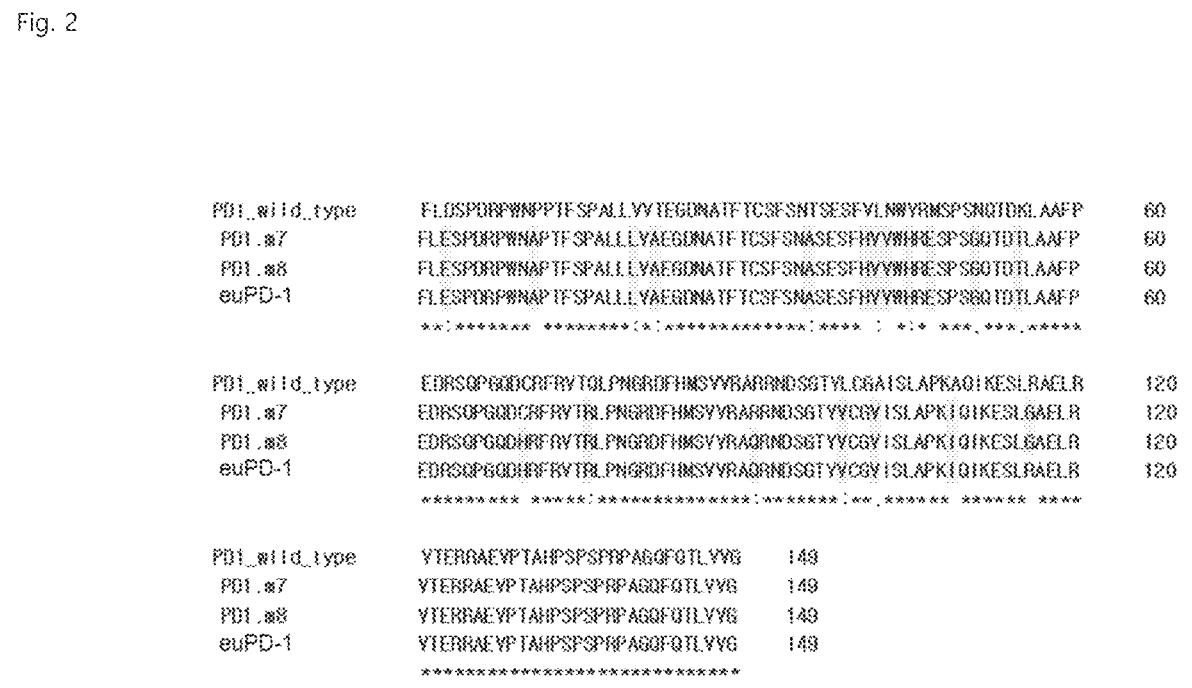

PD-1 Fc fusion proteins including PD-1 polypeptide variants were produced using a PD1-G$_4$S linker-Fc_pcDNA3.3 plasmid. The topology of human PD-1 protein is shown in Table 1. The sequences of human PD-1 and PD-1 polypeptide variants are shown in FIG. 1 and FIG. 2. Further, the mutations for each PD-1 polypeptide variant is listed in Table 2, wherein the amino acid residue number is relative to the full-length human PD-1 wild type sequence shown in FIG. 1 (SEQ ID NO: 11). PD-1 polypeptide variants were designed to include an extracellular domain (24-170) and a portion of a transmembrane domain (171-172) of the full-length human PD-1 wild type sequence shown in FIG. 1 (SEQ ID NO: 11). Specifically, the PD-1 Fc fusion proteins were produced using an animal cell expression vector pcDNA3.3 wherein restriction enzymes EcoRI and BamHI were inserted at restriction enzyme sites. Human PD-1 signal peptide (seq ID: Q15116, 1-23) was used for the signal peptide and 207aa-230aa IMGT allele IGHG1*03, 231aa-457aa IMGT allele IGHG2*01 was used for the Fc region. A DNA construct encoding a PD-1 Fc fusion protein is shown in FIG. 3.

TABLE 1

| Feature Key | Position(s) | Description |
|---|---|---|
| Topological domain | 24-170 | Extracellular |
| Transmembrane | 171-191 | Helical |
| Topological domain | 192-288 | Cytoplasmic |

TABLE 2

| Name Wild type PD-1 (SEQ ID NO: 11) | Mutation |
|---|---|
| PD-1.m7 | D26E, P34A, V43L, T45A, T59A, V64H, L65V, N66V, Y68H, M70E, N74G, K78T, Q99R, L122V, A125V, A132I, R139G |
| PD-1.m8 | D26E, P34A, V43L, T45A, T59A, V64H, L65V, N66V, Y68H, M70E, N74G, K78T, C93H, Q99R, R114Q, L122V, A125V, A132I, R139G |
| euPD-1 | D26E, P34A, V43L, T45A, T59A, V64H, L65V, N66V, Y68H, M70E, N74G, K78T, C93H, Q99R, R114Q, L122V, A125V, A132I |

Example 2—Analyzing and Characterizing PD-1 Polypeptide Variants

PD-1 polypeptide variants were inserted into plasmids and used to produce PD-1 Fe fusion proteins using Expi293 expression system (Invitrogen). The polypeptide variants were then purified using AktaPure (GE healthcare), and FibroPrismA column (GE healthcare, Cat #17-0618-01). The purified polypeptide variants were run through a desalting column (GE healthcare, Cat #17-1408-01) and protein concentration was measured using Multiskan GO (Thermo). Results are shown in Table 3.

TABLE 3

| PD-1 type | Concentration (mg/mL) | Volume (mL) | Yield (mg) | Ratio (wt/mt) |
|---|---|---|---|---|
| PD-1 wild type | 0.35 | 2 | 0.696 | 1 |
| PD-1.m7 | 0.11 | 2 | 0.224 | 0.322 |
| PD-1.m8 | 0.25 | 2 | 0.494 | 0.710 |
| euPD-1 | 0.33 | 2 | 0.662 | 0.951 |

Example 3—Analyzing PD-1 Polypeptide Variants with SDS-PAGE

Figure 4:
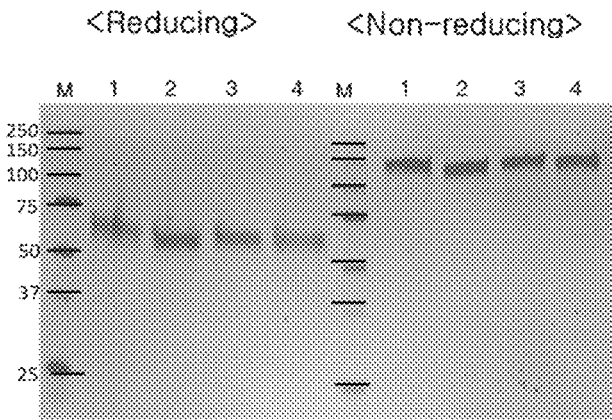
FIG. 4 shows SDS-PAGE results with PD-1 variant Fc fusion proteins, PD-1 Fc fusion protein (1), PD-1.m7 Fc fusion protein (2), PD-1.m8 Fc fusion protein (3), and euPD-1 Fc fusion protein (4).
Figures 5C, 5D:
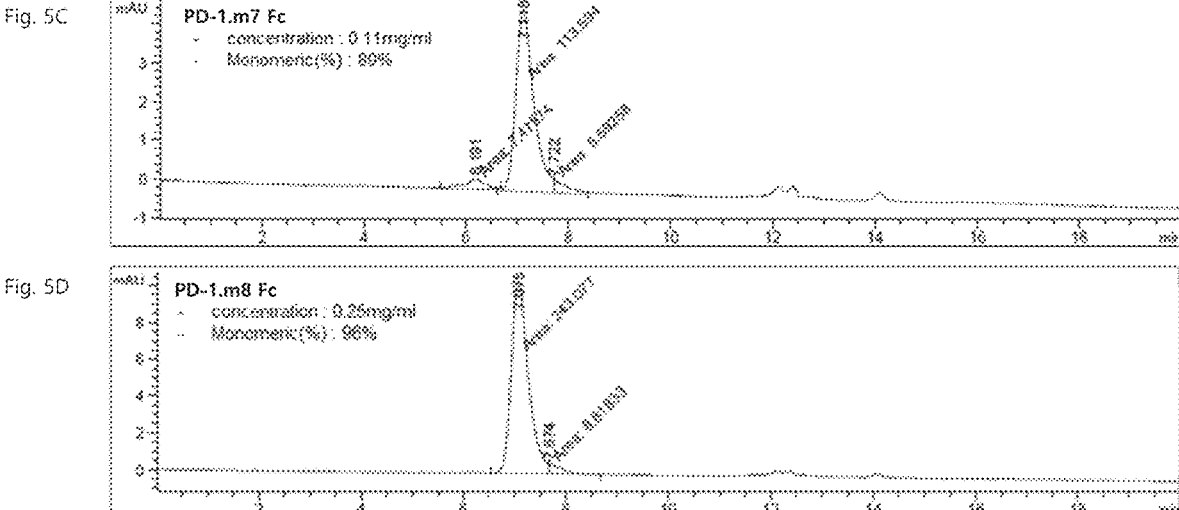
Figure 5E:
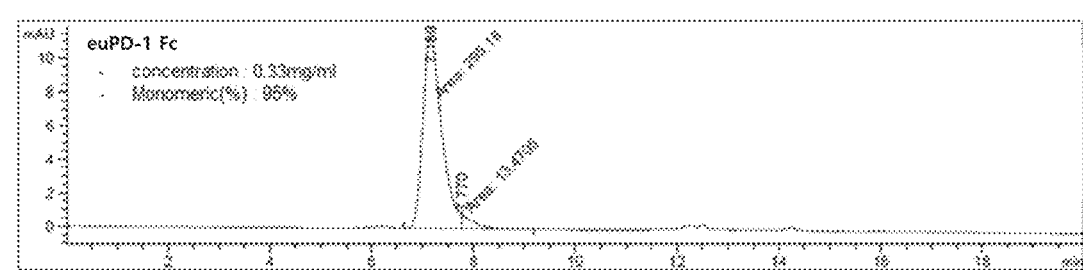

The PD-1 polypeptide variants were added to LDS sample buffer (Invitrogen, Cat #B0007), wherein a sample reducing agent (Invitrogen, Cat #B0004) was added to the reducing condition group and incubated for 10 minutes at 70° C. SDS running buffer (Bio-rad, Cat #1610732) was added to the prepared samples and the samples were run for 30 minutes using Mini-PROTEIN TGX Stain-Free Gel (Bio-rad, Cat #456-8096). Results were analyzed using Chemidoc (Bio-rad) (FIG. 4).

Example 4—Analyzing Affinity to PD-L1 Molecules

The affinity of PD-1 polypeptide variants to PD-L1 molecules was analyzed using surface plasmon resonance (SPR). The PD-1 polypeptide variants were diluted to a concentration of 2 ug/mL then fixed on CM5 chip (GE Healthcare, Cat #BR-1005-30). PD-L1 molecules (Sino, Cat #10084-H08H) were injected at concentrations 100, 50, 25, 12.5, 6.25, 3.125 nM with an association time of 150 seconds and dissociation time of 240 seconds. Biacore T200 (GE healthcare) was used to measure and analyze affinity of each PD-1 polypeptide variant. Results show PD-1 polypeptide variant euPD-1 has highest binding affinity to PD-L1 (Table 4).

TABLE 4

| PD-1 type | Affinity to PD-L1 | | |
|---|---|---|---|
| | ka (1/Ms) | kd (1/s) | K$_D$ (M) |
| PD-1 | 2.373E+5 | 0.01018 | 4.289E–8 |
| PD-1.m7 | 1.964E+6 | 0.002161 | 1.100E–9 |
| PD-1.m8 | 1.757E+6 | 0.001822 | 1.037E–9 |
| euPD-1 | 1.822E+6 | 0.001301 | 7.140E–10 |

Example 5—Size Exclusion Chromatography

The PD-1 polypeptide variants were analyzed using HPLC (Agilent Technologies, 1260 infinity II LC system)

and size exclusion column (Tosoh, TSKgel G3000 SWXL, 7.8×300 mm, Part No. 0008541, Column No. 004E04320E). Gel filtration standard (BIO-RAD, Cat. #151-1901) was used for the control (FIGS. 5A-5E).

Example 6—PD-1 Fusion Proteins Cell Binding Assay

Figure 6:
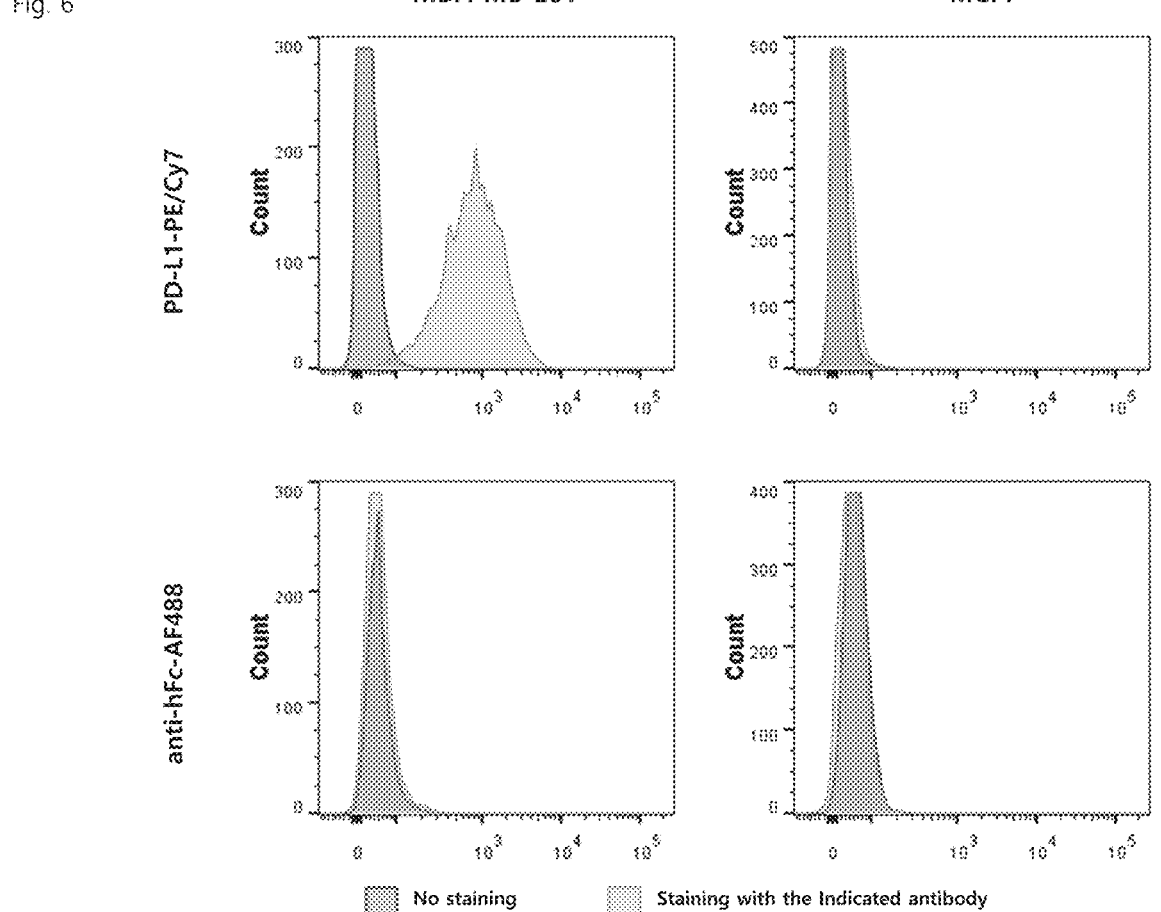
FIG. 6 shows the expression level of PD-L1 in PD-L1 high expressed cell line MDA-MB-231 (human breast cancer cell) and PD-L1 low expressed cell line MCF-7 (human breast cancer cell) cells.

PD-L1 high expressed cell line MDA-MB-231 (human breast cancer cell) and PD-L1 low expressed cell line MCF-7 (human breast cancer cell) cells were used. FIG. 6 shows the expression level of PD-L1 in each cell line. From FIG. 6 it is confirmed that PD-L1 is highly expressed in MDA-MB-231 and not in MCF7.

$1.5\times10^5$ cells were incubated at 4° C. for 20 minutes with antibody treatment. The treatment concentrations of euPD-1 Fc, PD-1 Fc, and Tecentriq (Genetech, atezolizumab, anti-PD-L1 antibody) were serial dilution doubled from 877.19 nM to a total of 12 points. After washing once with FACS washing buffer (0.5% FBS+0.1% $NaN_3$ in DPBS), anti-hFC-AF488 2nd antibody (Jackson ImmunoResearch) was treated at 1 µl/well for 20 minutes. After washing two additional times, FACS analysis was performed.

Figures 7A, 7B:
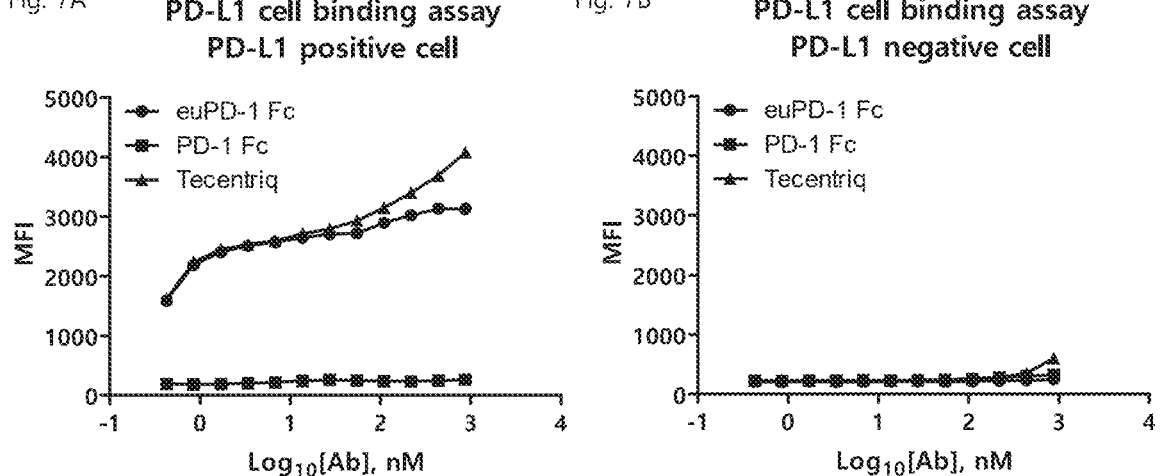
FIG. 7A shows FACS analysis of PD-1 Fc cell binding in PD-L1 positive cells.
FIG. 7B shows FACS analysis of PD-1 Fc cell binding in PD-L1 negative cells.

As a result of FACS analysis, it was confirmed that there was almost no background signal by the 2nd antibody. In FIG. 7A, PD-1 Fc did not bind to PD-L1 positive cells in the experimental concentration range, whereas euPD-1 Fc and Tecentriq were dose-dependently bound to PD-L1 positive cells. As a result of FACS analysis, in FIG. 7B, all three antibodies did not bind to PD-L1 negative cells.

Example 7—PD-1 Fusion Protein Antigen Binding Assay

Antigen binding assay was performed to confirm whether euPD-1 Fc binds to antigen PD-L1 or PD-L2.

The assay method was performed as shown in FIGS. 8A and 8C. Briefly, after coating PD-L1 antigen or PD-L2 antigen at a concentration of 1 µg/ml in a 96-well immuno-plate at 4° C. overnight, 150 µl of 1× assay buffer (Biolegend) was treated for 1 hour to block non-specific binding. Each of euPD-1 Fc, PD-1 Fc, and Tecentriq was treated with 100 µL and incubated for 2 hours. The treatment concentration on the antigen PD-L1-coated plate was serially diluted from 30 µg/mL to 3 times to make a total of 15 points, The treatment concentration on the antigen PD-L2 coated plate was serially diluted 3 times from 100 µg/mL to a total of 12 points. Anti-hFc-HRP (Biolegend) was treated with 100 µl at a concentration of 0.4 µg/mL. After incubation for 1 hour, color was developed with TMB, and after 3 minutes, the reaction was stopped using sulfuric acid. Washing was performed 3 times using washing buffer in all processes except for the process after TMB treatment, All processes except for the antigen coating process were carried out at room temperature. As a result of the experiment, as shown in FIG. 8B, binding of euPD-1 Fc and Tecentriq to antigen PD-L1 was confirmed in a dose-dependent manner. And in FIG. 8D, only PD-1 Fc bound to antigen PD-L2 in a dose-dependent manner, and euPD-1 Fc and Tecentriq did not bind.

Example 8—PD-1 Fusion Protein Blockade Bioassay

A blockade bioassay was performed to verify the binding inhibitory effect of PD-1 and PD-L1 (Bicytogen).

Figures 9A, 9B:
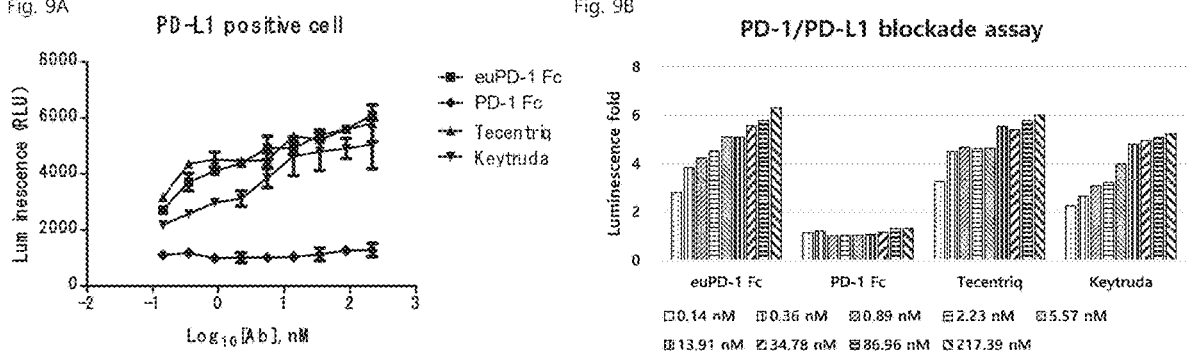
FIG. 9A and FIG. 9B show the results of the results of the PD-1/PD-L1 blockade bioassay in Example 8.

The bioassay product used (Promega, J1250) expresses luciferase under conditions in which the binding of PD-1 and PD-L1 is inhibited. The bioassay and luciferase assay followed Promega protocol. Target cells were seeded at $4\times10^4$ cells/100 µL/well in a 96 well white plate. After overnight incubation in a 37° C. $CO_2$ incubator, antibodies and effector cells were treated. As the antibody, euPD-1 Fc, PD-1 Fc, Tecentriq, and Keytruda (Merck, pembrolizumab, anti-PD-1 antibody) were used. The treatment concentration was serially dilution 2.5 times from 217.39 nM to make a total of 10 points. After 6 hours of incubation in a 37° C. $CO_2$ incubator, luciferin was treated and luciferase assay was performed. As a result of luciferase assay, as shown in FIG. 9A, euPD-1 Fc, Tecentriq, and Keytruda showed inhibitory effects in a dose-dependent manner, and, as shown in FIG. 9B, euPD-1 Fc showed more than 2.4 to 4.9 times more inhibitory effect than PD-1 Fc.

Example 9—PD-1 Fusion Protein In Vivo Efficacy Study

To verify the efficacy of euPD-1 Fc, a tumor growth inhibition in vivo study was performed. The experiment was performed using a female C57BL/6 mouse that knocked-in hPD-1.

As the tumor cells, MC38 cells expressing human PD-L1 were used as shown in FIGS. 10, and $8\times10^6$ tumor cells per individual were subcutaneously administered. After one week of administration, the tumor size was measured and the administration groups were allocated so that the mean and standard deviation were similar (i.e., about 100 $mm^3$). Antibodies euPD-1 Fc, PD-1 Fc, and Tecentriq three were injected by i.v. As a negative control, the excipient DPBS (Gibco) was used. The antibody dose was set to 5 mg/kg and 2 mg/kg based on euPD-1 Fc, and 8.77 µM concentration was used for PD-1 fc and tecentriq 5 mg/kg in consideration of molecular weight. The administration was carried out at 100 µl, and was administered 5 times at 3-day intervals. The tumor size was also measured at 3-day or 4-day intervals, and the tumor size was measured until 2 days after the last administration. In addition, blood was collected on the day of the end of the experiment to confirm toxicity, and the concentrations of ALT (alanine aminotransferase), AST (aspartate aminotransferase), BUN (blood urea nitrogen), and T-BIL (total Bilirubin) were checked using a biochemical analyzer.

As a result of tumor size observation, as shown in FIG. 11 A and FIG. 11, both euPD-1 Fc (8.77 µM) and tecentriq (8.77 µM) inhibited tumor growth compared to administration of negative control; PD-1 Fc (8.77 µM) showed growth similar to that of the negative control. In addition, as shown in FIG. 11C and FIG. 11D, euPD-1 Fc reduced the tumor size by 33.9% compared to the negative control administration in the low concentration (2 mg/kg) administration group, A 66.1% tumor size reduction was observed in the group administered with a high grade (5 mg/kg), showing a dose-dependent inhibitory effect.

Figures 12A, 12B, 12C, 12D:
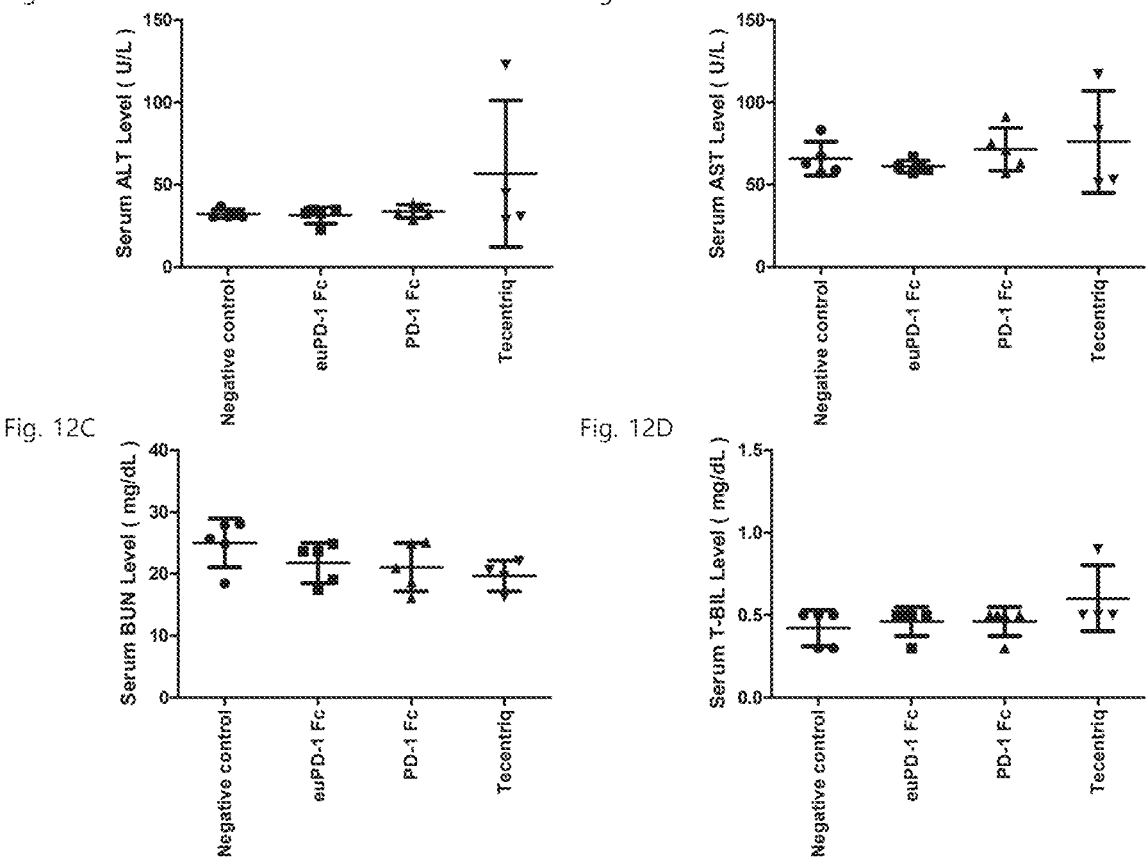
FIG. 12 shows the liver toxicity index analysis in Example 9 (ALT: 17-77 U/L (FIG. 12A and FIG. 12E), AST: 54-298 U/L (FIG. 12B and FIG. 12F), BUN: 8-33 mg/dL (FIG. 12C and FIG. 12G), T-BIL: 8-33 mg/dL (FIG. 12D and FIG. 12H)).
Figures 12E, 12F, 12G, 12H:
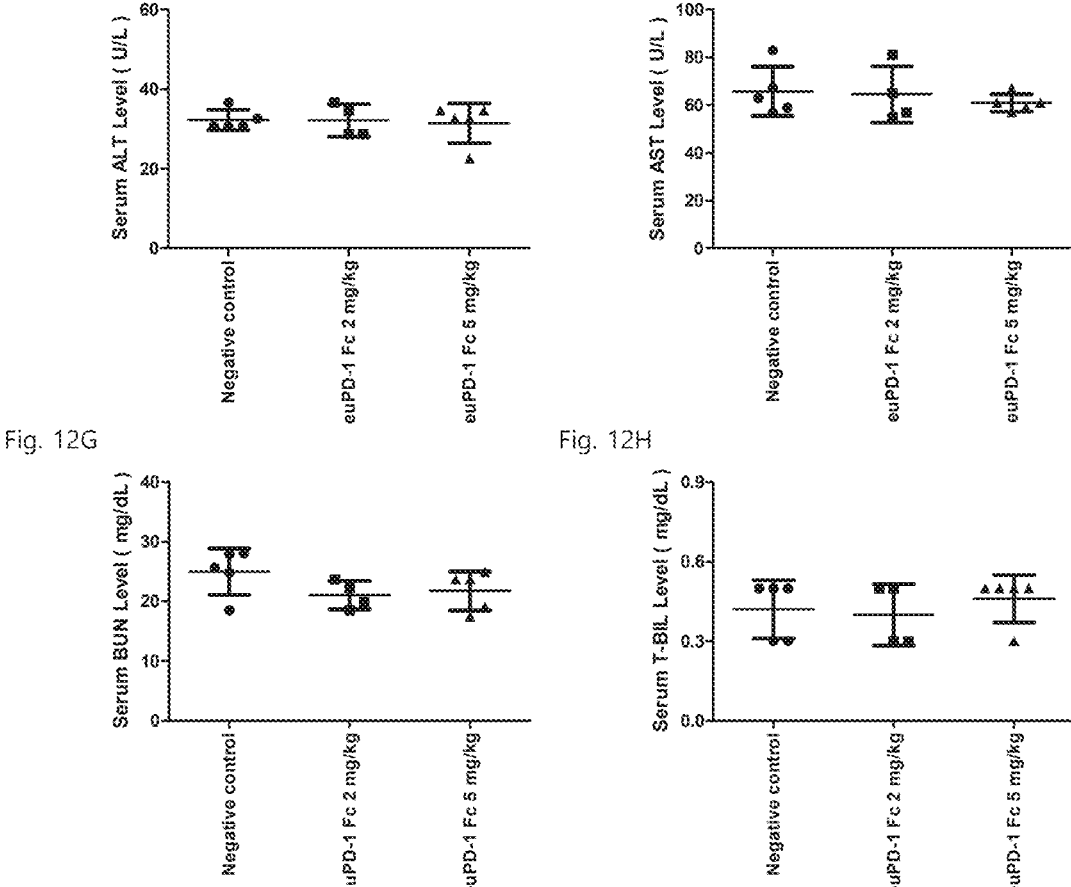

Further, a liver toxicity index analysis was performed and shown in FIG. 12. As shown in FIG. 12 for the liver toxicity index analysis, in the euPD-1 Fc administration group, all four indicators were in the normal range (ALT: 17-77 U/L (FIG. 12A and FIG. 12E), AST: 54-298 U/L (FIG. 12B and FIG. 12F), BUN: 8-33 mg/dL (FIG. 12C and FIG. 12G), T-BIL: 8-33 mg/dL (FIG. 12D and FIG. 12H)), no hepato-toxicity was confirmed within the experimental conditions.

Thus, it was confirmed that the fusion proteins and bispecific antibodies of the present invention comprising euPD-1 and IgG1 variants displayed no hepatotoxicity. In addition, the antibodies of the present invention lack ADCC and CDC effects.

Figure 13:
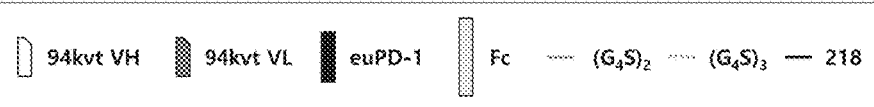
FIG. 13 shows Fc fusion BsAB using euPD-1 and anti-4-1BB antibody described in Example 10.
Figure 14:
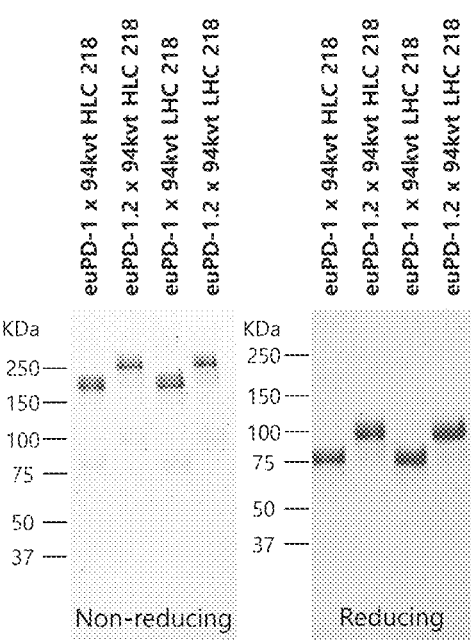
FIG. 14 shows SDS-PAGE results with Fc fusion BsAB using euPD-1 and anti-4-1BB antibody described in Example 10.

Example 10—Design, Production, and Characterization of PD-1 Fusion Protein euPD-1 BsAb Fc fusion BsAb using euPD-1 and anti-4-1BB antibody was designed as shown in FIG. 13. A $(G_4S)_2$ linker was used to link euPD-1 and Fc, and Fc region modified with IgG1 was used for the Fc region used for BsAb. (L234A, L235A, K322A, D356E, L358M).

BsAb in the form of linking two euPD-1s was also designed; to link two euPD-1s, a $(G_4S)_3$ linker was used and named euPD-1.2.

On the C-terminal side, the anti-4-1BB antibody was bound to Fc in the form of scFv; at this time, it was linked with a $(G_4S)_2$ linker, and two types of scFvs for the anti-4-1BB antibody, VH-218 linker-VL (HLC 218) and VL-218 linker-VH (LHC 218), were used.

The constructs in Table 5 or FIG. 13 were produced. Also provided are the sequences referred to above.

TABLE 5

| Seq ID No. | Name | Amino acid sequence |
|---|---|---|
| 12 | euPD-1 x 94kvt HLC 218 | FLESPDRPWNAPTFSPALLLVAEGDNATFTCSFSNASESFHVV WHRESPSGQTDTLAAFPEDRSQPGQDHRFRVTRLPNGRDFH MSVVRAQRNDSGTYVCGVISLAPKIQIKESLRAELRVTERRA EVPTAHPSPSPRPAGQFQTLVVGASGGGGSGGGGSDKTHTCP PCPAPEAAGGPSVFLFPPKPKDTLMISRTPEVTCVVVDVSHE DPEVKFNWYVDGVEVHNAKTKPREEQYNSTYRVVSVLTVL HQDWLNGKEYKCAVSNKALPAPIEKTISKAKGQPREPQVYT LPPSREEMTKNQVSLTCLVKGFYPSDIAVEWESNGQPENNY KTTPPVLDSDGSFFLYSKLTVDKSRWQQGNVFSCSVMHEAL HNHYTQKSLSLSPGGGGGSGGGGSQVQLVQSGAEVKKPGAS VKLSCKASGYTFSSYWMHWVRQAPGQGLEWIGEINPGNGH TNYNEKFKSRVTMTRDTSTSTAYMELSSLRSEDTAVYYCAR SFKTARAFAYWGQGTLVTVSSGSTSGSGKPGSGEGSTKGDIV MTQSPAFLSVTPGEKVTITCRASQTISDYLHWYQQKPDQAPK LLIKYASQSISGIPSRFSGSGSGTDFTFTISSLEAEDAATYYCQ DGHSWPPTFGQGTKLEIK |
| 13 | euPD-1.2 x 94kvt HLC 218 | FLESPDRPWNAPTFSPALLLVAEGDNATFTCSFSNASESFHVV WHRESPSGQTDTLAAFPEDRSQPGQDHRFRVTRLPNGRDFH MSVVRAQRNDSGTYVCGVISLAPKIQIKESLRAELRVTERRA EVPTAHPSPSPRPAGQFQTLVVGGGGGSGGGGSGGGGSFLES PDRPWNAPTFSPALLLVAEGDNATFTCSFSNASESFHVVWHR ESPSGQTDTLAAFPEDRSQPGQDHRFRVTRLPNGRDFHMSV VRAQRNDSGTYVCGVISLAPKIQIKESLRAELRVTERRAEVPT AHPSPSPRPAGQFQTLVVGASGGGGSGGGGSDKTHTCPPCPA PEAAGGPSVFLFPPKPKDTLMISRTPEVTCVVVDVSHEDPEV KFNWYVDGVEVHNAKTKPREEQYNSTYRVVSVLTVLHQD WLNGKEYKCAVSNKALPAPIEKTISKAKGQPREPQVYTLPPS REEMTKNQVSLTCLVKGFYPSDIAVEWESNGQPENNYKTTP PVLDSDGSFFLYSKLTVDKSRWQQGNVFSCSVMHEALHNHY TQKSLSLSPGGGGGSGGGGSQVQLVQSGAEVKKPGASVKLS CKASGYTFSSYWMHWVRQAPGQGLEWIGEINPGNGHTNYN EKFKSRVTMTRDTSTSTAYMELSSLRSEDTAVYYCARSFKTA RAFAYWGQGTLVTVSSGSTSGSGKPGSGEGSTKGDIVMTQS PAFLSVTPGEKVTITCRASQTISDYLHWYQQKPDQAPKLLIK YASQSISGIPSRFSGSGSGTDFTFTISSLEAEDAATYYCQDGHS WPPTFGQGTKLEIK |
| 14 | euPD-1 x 94kvt LHC 218 | FLESPDRPWNAPTFSPALLLVAEGDNATFTCSFSNASESFHVV WHRESPSGQTDTLAAFPEDRSQPGQDHRFRVTRLPNGRDFH MSVVRAQRNDSGTYVCGVISLAPKIQIKESLRAELRVTERRA EVPTAHPSPSPRPAGQFQTLVVGASGGGGSGGGGSDKTHTCP PCPAPEAAGGPSVFLFPPKPKDTLMISRTPEVTCVVVDVSHE DPEVKFNWYVDGVEVHNAKTKPREEQYNSTYRVVSVLTVL HQDWLNGKEYKCAVSNKALPAPIEKTISKAKGQPREPQVYT LPPSREEMTKNQVSLTCLVKGFYPSDIAVEWESNGQPENNY KTTPPVLDSDGSFFLYSKLTVDKSRWQQGNVFSCSVMHEAL HNHYTQKSLSLSPGGGGGSGGGGSDIVMTQSPAFLSVTPGEK VTITCRASQTISDYLHWYQQKPDQAPKLLIKYASQSISGIPSRF SGSGSGTDFTFTISSLEAEDAATYYCQDGHSWPPTFGQGTKL EIKGSTSGSGKPGSGEGSTKGQVQLVQSGAEVKKPGASVKLS CKASGYTFSSYWMHWVRQAPGQGLEWIGEINPGNGHTNYN EKFKSRVTMTRDTSTSTAYMELSSLRSEDTAVYYCARSFKTA RAFAYWGQGTLVTVSS |
| 15 | euPD-1.2 x 94kvt LHC 218 | FLESPDRPWNAPTFSPALLLVAEGDNATFTCSFSNASESFHVV WHRESPSGQTDTLAAFPEDRSQPGQDHRFRVTRLPNGRDFH MSVVRAQRNDSGTYVCGVISLAPKIQIKESLRAELRVTERRA EVPTAHPSPSPRPAGQFQTLVVGGGGGSGGGGSGGGGSFLES PDRPWNAPTFSPALLLVAEGDNATFTCSFSNASESFHVVWHR ESPSGQTDTLAAFPEDRSQPGQDHRFRVTRLPNGRDFHMSV |

TABLE 5-continued

| Seq ID No. | Name | Amino acid sequence |
|---|---|---|
| | | VRAQRNDSGTYVCGVISLAPKIQIKESLRAELRVTERRAEVPT<br>AHPSPSPRPAGQFQTLVVGASGGGGGGGGSDKTHTCPPCPA<br>PEAAGGPSVFLFPPKPKDTLMISRTPEVTCVVVDVSHEDPEV<br>KFNWYVDGVEVHNAKTKPREEQYNSTYRVVSVLTVLHQD<br>WLNGKEYKCAVSNKALPAPIEKTISKAKGQPREPQVYTLPPS<br>REEMTKNQVSLTCLVKGFYPSDIAVEWESNGQPENNYKTTP<br>PVLDSDGSFFLYSKLTVDKSRWQQGNVFSCSVMHEALHNHY<br>TQKSLSLSPGGGGGSGGGGSDIVMTQSPAFLSVTPGEKVTITC<br>RASQTISDYLHWYQQKPDQAPKLLIKYASQSISGIPSRFSGSG<br>SGTDFTFTISSLEAEDAATYYCQDGHSWPPTFGQGTKLEIKGS<br>TSGSGKPGSGEGSTKGQVQLVQSGAEVKKPGASVKLSCKAS<br>GYTFSSYWMHWVRQAPGQGLEWIGEINPGNGHTNYNEKFK<br>SRVTMTRDTSTSTAYMELSSLRSEDTAVYYCARSFKTARAF<br>AYWGQGTLVTVSS |
| 16 | Fc | DKTHTCPPCPAPEAAGGPSVFLFPPKPKDTLMISRTPEVTCVV<br>VDVSHEDPEVKFNWYVDGVEVHNAKTKPREEQYNSTYRVV<br>SVLTVLHQDWLNGKEYKCAVSNKALPAPIEKTISKAKGQPR<br>EPQVYTLPPSREEMTKNQVSLTCLVKGFYPSDIAVEWESNGQ<br>PENNYKTTPPVLDSDGSFFLYSKLTVDKSRWQQGNVFSCSV<br>MHEALHNHYTQKSLSLSPG |
| 17 | 94kvt VH | QVQLVQSGAEVKKPGASVKLSCKASGYTFSSYWMHWVRQ<br>APGQGLEWIGEINPGNGHTNYNEKFKSRVTMTRDTSTSTAY<br>MELSSLRSEDTAVYYCARSFKTARAFAYWGQGTLVTVSS |
| 18 | 94kvt VL | DIVMTQSPAFLSVTPGEKVTITCRASQTISDYLHWYQQKPDQ<br>APKLLIKYASQSISGIPSRFSGSGSGTDFTFTISSLEAEDAATYY<br>CQDGHSWPPTFGQGTKLEIK |
| 19 | $(G_4S)_2$ | GGGGSGGGGS |
| 20 | $(G_4S)_3$ | GGGGSGGGGSGGGGS |
| 21 | 218 | GSTSGSGKPGSGEGSTKG |
| 22 | 94kvt HLC 218 | QVQLVQSGAEVKKPGASVKLSCKASGYTFSSYWMHWVRQ<br>APGQGLEWIGEINPGNGHTNYNEKFKSRVTMTRDTSTSTAY<br>MELSSLRSEDTAVYYCARSFKTARAFAYWGQGTLVTVSSGS<br>TSGSGKPGSGEGSTKGDIVMTQSPAFLSVTPGEKVTITCRASQ<br>TISDYLHWYQQKPDQAPKLLIKYASQSISGIPSRFSGSGSGTD<br>FTFTISSLEAEDAATYYCQDGHSWPPTFGQGTKLEIK |
| 23 | 94kvt LHC 218 | DIVMTQSPAFLSVTPGEKVTITCRASQTISDYLHWYQQKPDQ<br>APKLLIKYASQSISGIPSRFSGSGSGTDFTFTISSLEAEDAATYY<br>CQDGHSWPPTFGQGTKLEIKGSTSGSGKPGSGEGSTKGQVQL<br>VQSGAEVKKPGASVKLSCKASGYTFSSYWMHWVRQAPGQG<br>LEWIGEINPGNGHTNYNEKFKSRVTMTRDTSTSTAYMELSSL<br>RSEDTAVYYCARSFKTARAFAYWGQGTLVTVSS |

Transient transfection was performed into Expi293F cells to produce euPD-1 BsAbs (bispecific antibodies); purification was carried out by protein A column.

Figures 15A, 15B, 15C:
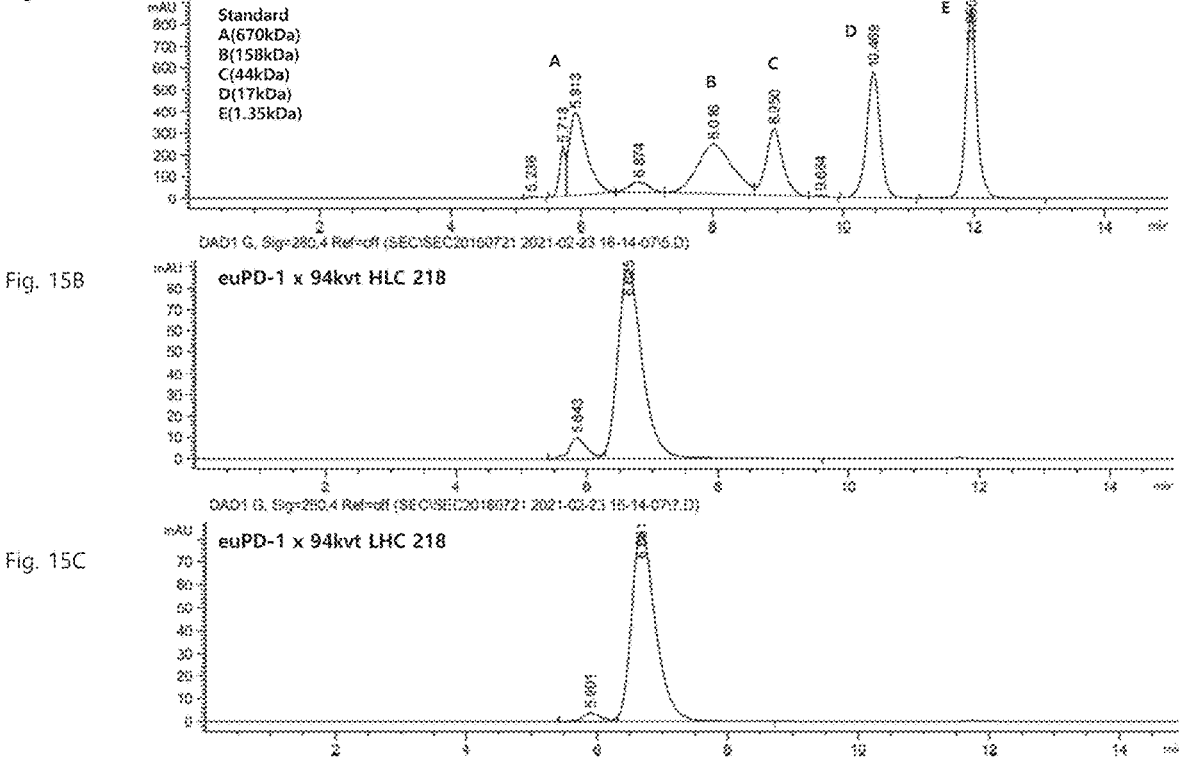
FIG. 15A is a standard curve.
FIG. 15B is euPD-1×94kvt HLC 218.
FIG. 15C is euPD-1×94kvt LHC 218.
Figures 15D, 15E:
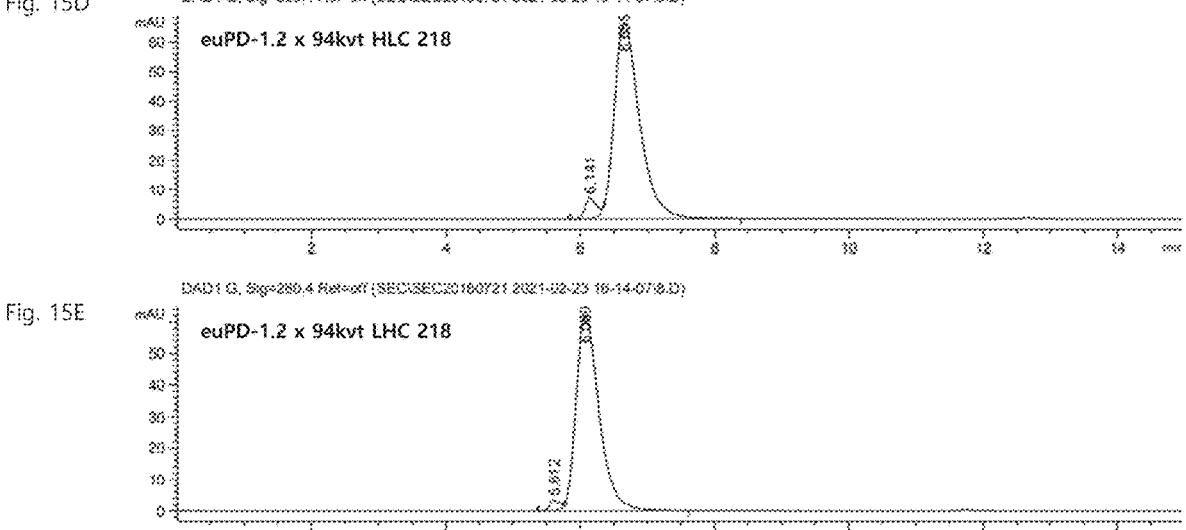
FIG. 15D is euPD-1.2×94kvt HLC 218.
FIG. 15E is euPD-1.2×94kvt LHC 218.

As a result of SDS-PAGE analysis, in the non-reducing condition, euPD-1×94kvt HLC 218 and euPD-1×94kvt LHC 218 with one euPD-1 were observed to be about 160 kDa; in the reducing condition, it was observed to be about 80 kDa. The euPD-1 doubled form, euPD-1.2×94 kvt HLC 218 and euPD-1.2×94 kvt LHC 218, is observed to be about 250 kDa; in the reducing condition, it was observed to be about 125 kDa. As a result of size exclusion chromatograpy analysis, a single peak with a purity of 90% or more was observed (see FIG. 15 where FIG. 15A is a standard curve, FIG. 15B is euPD-1×94kvt HLC 218, FIG. 15C is euPD-1×94kvt LHC 218, FIG. 15D is euPD-1.2×94kvt HLC 218, and FIG. 15E is euPD-1.2×94kvt LHC 218).

Figure 16:
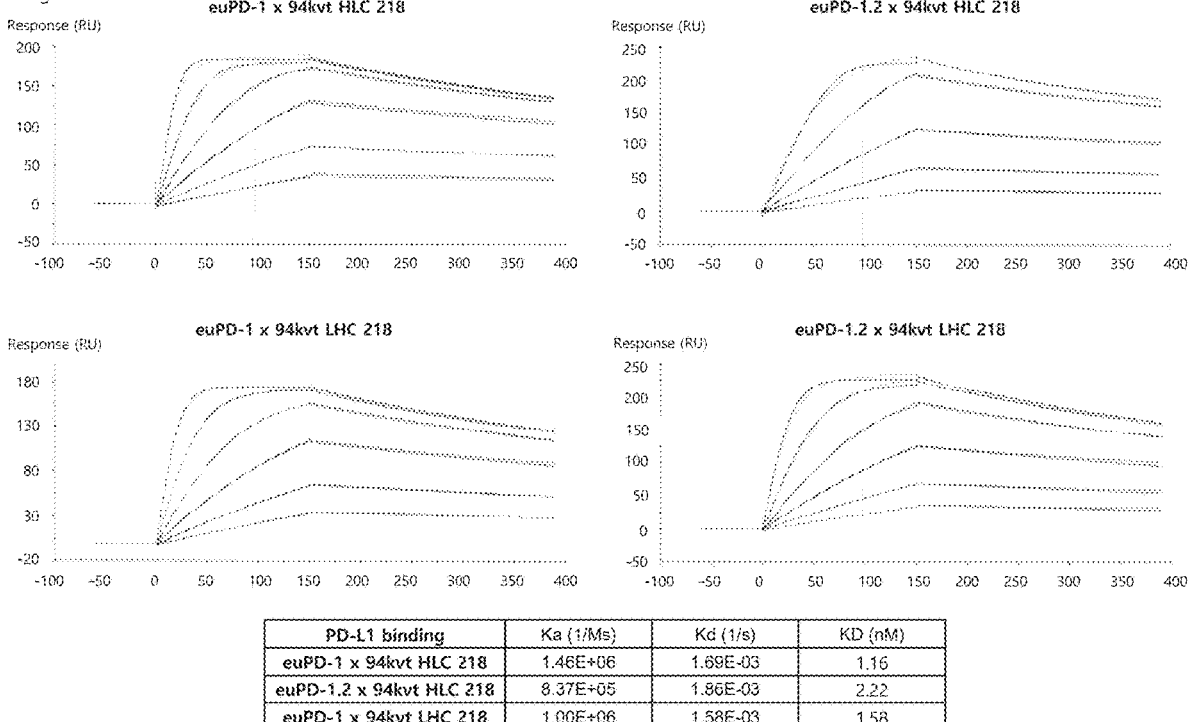
FIG. 16 shows the SPR result of the euPD-1 BsAB constructs in Example 10.

Surface plasmon resonance (SPR) analysis similar to as described in Example 4 was followed. Specifically, 25 μg/ml anti-human Fc antibody was immobilized on the CM5 chip. 25 μg/ml anti-human Fc antibody was immobilized on the CM5 chip. After that, 4 types of euPD-1 BsAb were caused to flow at a flow rate of 10 μg/ml and 10 μl/min for 60 seconds to capture, and KD analysis was performed using 100, 50, 25, 12.5, 3.25, 3.125, 0 nM of PD-L1 antigen. FIG. 16 shows the SPR result of the euPD-1 BsAb constructs.

Example 11—Antigen Binding Assay with euPD-1 BsAb Constructs

To check whether euPD-1 BsAbs binds to antigen PD-L1, an antigen binding assay was performed.

Figure 17A:
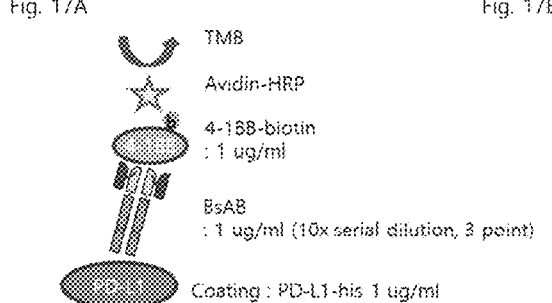
FIG. 17A shows the antigen binding assay method used in Example 11.

The assay method was performed as shown in FIG. 17A. Briefly, after coating PD-L1 antigen at a concentration of 1 μg/ml in a 96-well immunoplate at 4° C. with overnight, 150 μl of Ix assay buffer (Biolegend) was treated for 1 hour to block non-specific binding. euPD-1 BsAb was incubated for 2 hours after treatment with 100 μL. The treatment concentration was serially diluted 10 times from 10 μg/mL to a total of 3 points. 100 μl of biontinylated 4-1BB at a concentration of 1 μg/ml was treated for 1 hour. Avidin-HRP (Bioglend) was treated with 100 μl at the concentration shown in the protocol for 30 minutes. After color development with TMB, the reaction was stopped with sulfuric acid after 3 minutes. Washing was performed 3 times using washing buffer in all processes except for the process after TMB treatment; except for the PD-L1 coating process, all processes were carried out at room temperature.

Figure 17B:
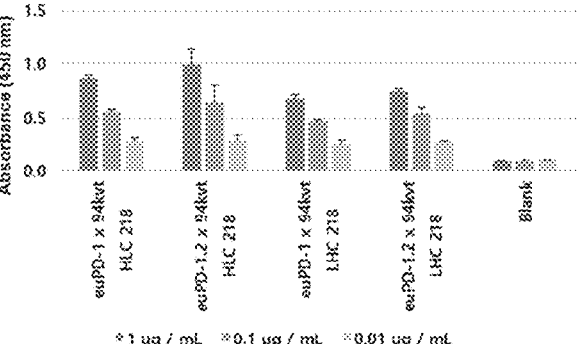
FIG. 17B shows the antigen binding result in Example 11.

As a result of the experiment, as shown FIG. 17B, binding of euPD-1 BsAb to antigen PD-L1 was confirmed in a dose-dependent manner.

Example 12-4-1BB/PD-1 Combination Bioassay

In order to verify the effect of inhibiting the binding of PD-1 and PD-L1 and the effect of 4-1BB activity, a 4-1BB/PD-1 combination bioassay was performed.

For this experiment, the bioassay product (Promega, CS1978110) is an assay system which expresses luciferase when 4-1BB is activated by 4-1BB antibody stimulation and when the PD-1/PD-L1 interaction inhibits at the same time. The bioassay and luciferase assay followed Promega protocol. MDA-MB-231 cells expressing PD-L1 were seeded at $4×10^4$ cells/100 µL/well in a 96 well white plate. After O/N incubation in a 37° C. $CO_2$ incubator, antibodies and PD1+ 4-1BB effector cells were treated. As antibodies, euPD-1×94 kvt HLC 218 and euPD-1×94 kvt LHC 218 were used. The treatment concentration was serially dilution from 60 ng/ml to 4 times to make a total of 4 points. After 6 hours of incubation in a 37° C. $CO_2$ incubator, luciferin was treated and luciferase assay was performed.

Figure 18:
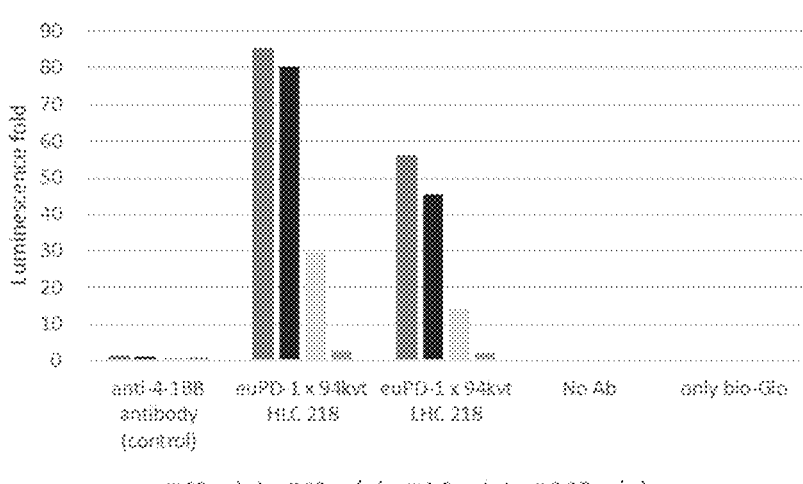
FIG. 18 shows the results of the results of the 4-1BB/PD-1 combination bioassay in Example 12.

As a result of luciferase assay, as shown in FIG. 18, euPD-1×94 kvt HLC 218 and euPD-1×94 kvt LHC 218 activated 4-1BB while inhibiting PD-1/PD-L1 in a dose-dependent manner.

What is claimed is:

1. A programmed cell death 1 (PD-1) polypeptide variant comprising the amino acid sequence of residues 24 to 172 of SEQ ID NO: 11,
   wherein the PD-1 polypeptide variant comprises:
      an extracellular domain that binds specifically to programmed cell death 1 ligand (PD-L1); and
      a transmembrane domain or a fragment thereof,
      wherein the PD-1 polypeptide variant has a mutation at T45, V64, N66, and Q99; and at least at one residue selected from the group consisting of D26, P34, and V43; and may further have a mutation at one or more residue selected from the group consisting of T59, L65, Y68, M70, N74, K78, L122, A125 and A132, and the PD-1 polypeptide has a C or H at residue 93.

2. The PD-1 polypeptide variant of claim 1,
   wherein the PD-1 polypeptide variant comprises the amino acid sequence of SEQ ID NO: 4, SEQ ID NO: 6, or SEQ ID NO: 8.

3. The PD-1 polypeptide variant of claim 1, wherein the transmembrane domain comprises at least two amino acid residues.

4. The PD-1 polypeptide variant of claim 1, wherein the polypeptide variant has increased binding affinity to a PD-L1 molecule as compared to a wild-type PD-1 polypeptide.

5. The PD-1 polypeptide variant of claim 4, wherein the polypeptide variant has a binding affinity ($K_D$) for a PD-L1 molecule of about $1×10^{-8}$ to $1×^{-10}$M.

6. A programmed cell death 1 (PD-1) polypeptide variant comprising the amino acid sequence of residues 24 to 172 of SEQ ID NO: 11, wherein the PD-1 polypeptide variant has a mutation at T45, V64, N66, and Q99; and at least at one residue selected from the group consisting of D26, P34, and V43; and may further have a mutation at one or more residue selected from the group consisting of T59, Y68, M70, N74, K78, L122, A125 and A132, and the PD-1 polypeptide has a C or H at residue 93.

7. The PD-1 polypeptide variant of claim 6, wherein said variant comprises a mutation at D26, P34, V43, T59, L65, Y68, M70, N74, K78, L122, A125, and A132; and further comprises a mutation at R139.

8. The PD-1 polypeptide variant of claim 6, wherein said variant comprises a mutation at D26, P34, V43, T59, L65, Y68, M70, N74, K78, L122, A125, A132; and further comprises a mutation at C93, R114, and R139.

9. The PD-1 polypeptide variant of claim 6, wherein the PD-1 polypeptide variant has at least at one mutation selected from the group consisting of D26E, P34A and V43L, and at least at one residue selected from the group consisting of T45A, V64H and N66V;
   and the PD-1 polypeptide variant optionally has at least one additional mutation selected from the group consisting of T59A, L65V, Y68H, M70E, N74G, K78T, Q99R, L122V, A125V and A132I,
   and may further have a mutation at one or more mutation selected from the group consisting of R114Q, and R139G,
   and the PD-1 polypeptide has a C or H at residue 93.

10. A PD-1 Fc fusion protein comprising:
    an immunoglobulin Fc region; and
    a PD-1 polypeptide variant of claim 1 linked by a peptide bond or a peptide linker sequence to the carboxy-terminus of the immunoglobulin Fc region.

11. The PD-1 Fc fusion protein of claim 10, wherein the immunoglobulin Fc region comprises an amino acid sequence having 95% or more sequence identity to SEQ ID NO: 10 or SEQ ID NO: 16.

12. The PD-1 Fc fusion protein of claim 10, wherein two copies of PD-1 polypeptide variant are present, which may be the same or different, and are linked by a peptide linker sequence.

13. The PD-1 Fc fusion protein of claim 10, wherein the fusion protein has increased binding affinity to a PD-L1 molecule as compared to a wild-type PD-1 polypeptide.

14. The PD-1 Fc fusion protein of claim 13, wherein the fusion protein has a binding affinity ($K_D$) for a PD-L1 molecule of about $1\times10^{-8}$ to $1\times10^{-10}$ M.

15. A PD-1 Fc fusion protein
comprising: an immunoglobulin Fc region; and
a PD-1 polypeptide variant of claim 6 linked by a peptide bond or a peptide linker sequence to the carboxy-terminus of the immunoglobulin Fc region.

16. The PD-1 Fc fusion protein of claim 15, wherein two copies of PD-1 polypeptide variant are present, which may be the same or different, and are linked by a peptide linker sequence.

17. A nucleic acid comprising:
a sequence encoding a PD-1 polypeptide variant of claim 6.

18. The nucleic acid of claim 17, further comprising:
a sequence encoding an immunoglobulin Fc region, wherein the sequence encoding the immunoglobulin Fc region comprises SEQ ID NO: 9.

19. An expression vector comprising the nucleic acid of claim 17.

20. The vector of claim 19, wherein the vector is a viral vector.

21. A pharmaceutical composition comprising:
the PD-1 polypeptide variant of claim 1 or a fusion protein comprising an immunoglobulin Fc region and said PD-1 polypeptide variant linked by a peptide bond or a peptide linker sequence to the carboxy-terminus of the immunoglobulin Fc region; and
a pharmaceutically acceptable carrier.

22. A method of treating a disease or a condition in a subject in need thereof, the method comprising:
administering to the subject the pharmaceutical composition of claim 21, thereby treating a disease or a condition.

23. The method of claim 22, wherein the subject has cancer.

24. The method of claim 23, wherein the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

25. The method of claim 22, wherein when the pharmaceutical composition comprises said fusion protein, decreased or no antibody-dependent cellular cytotoxicity (ADCC) and/or complement-dependent cytotoxicity (CDC) effects are observed.

26. The method of claim 22, wherein when the pharmaceutical composition comprises said fusion protein, decreased or no hepatotoxicity is observed.

27. A pharmaceutical composition comprising:
the PD-1 polypeptide variant of claim 6 or a fusion protein comprising an immunoglobulin Fc region and said PD-1 polypeptide variant linked by a peptide bond or a peptide linker sequence to the carboxy-terminus of the immunoglobulin Fc region; and
a pharmaceutically acceptable carrier.

28. A method of treating a disease or a condition in a subject in need thereof, the method comprising:
administering to the subject the pharmaceutical composition of claim 27, thereby treating a disease or a condition.

29. The method of claim 28, wherein the subject has cancer.

30. The method of claim 29, wherein the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

31. The method of claim 28, wherein when the pharmaceutical composition comprises said fusion protein, decreased or no antibody-dependent cellular cytotoxicity (ADCC) and/or complement-dependent cytotoxicity (CDC) effects are observed.

32. The method of claim 28, wherein when the pharmaceutical composition comprises said fusion protein, decreased or no hepatotoxicity is observed.

33. A bispecific antibody
comprising: an immunoglobulin Fc region;
a PD-1 polypeptide variant of claim 1 linked by a peptide bond or a peptide linker sequence to the N-terminus of the immunoglobulin Fc region; and
a scFv for the anti-4-1BB antibody linked by a peptide bond or a peptide linker sequence to the C-terminus of the immunoglobulin Fc region, wherein the scFv for the anti-4-1BB antibody comprises an amino acid sequence having 95% or more sequence identity to an amino acid sequence comprising SEQ ID NO: 17 and 18 linked by a peptide bond or a peptide linker sequence.

34. The bispecific antibody of claim 33, wherein the immunoglobulin Fc region comprises an amino acid sequence having 95% or more sequence identity to SEQ ID NO: 10 or SEQ ID NO: 16.

35. The bispecific antibody of claim 33, wherein the PD-1 polypeptide or the scFv or both are linked to the immunoglobulin Fc region by a peptide linker selected from the group consisting of SEQ ID NO: 19, SEQ ID NO: 20, and SEQ ID NO: 21.

36. The bispecific antibody of claim 33, wherein the scFv for the anti-4-1BB antibody comprises a sequence that is at least 90% identical to SEQ ID NO: 22 or SEQ ID N0:23.

37. The bispecific antibody of claim 33, wherein the scFv for the anti-4-1BB antibody comprises SEQ ID NO: 22 or SEQ ID NO: 23.

38. The bispecific antibody of claim 33, wherein the bispecific antibody has increased binding affinity to a PD-L1 molecule as compared to a wild-type PD-1 polypeptide and specific binding affinity to 4-1BB.

39. A pharmaceutical composition comprising:
the bispecific antibody of claim 33; and
a pharmaceutically acceptable carrier.

40. A method of treating a disease or a condition in a subject in need thereof, the method comprising:

administering to the subject the pharmaceutical composition of claim 39, thereby treating a disease or a condition.

41. The method of claim 40, wherein the subject has cancer.

42. The method of claim 41, wherein the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

43. The method of claim 40, wherein when the pharmaceutical composition comprises said fusion protein, decreased or no antibody-dependent cellular cytotoxicity (ADCC) and/or complement-dependent cytotoxicity (CDC) effects are observed.

44. The method of claim 40, wherein when the pharmaceutical composition comprises said fusion protein, decreased or no hepatotoxicity is observed.

45. A bispecific antibody comprising:
an immunoglobulin Fc region;
a PD-1 polypeptide variant of claim 6 linked by a peptide bond or a peptide linker sequence to the N-terminus of the immunoglobulin Fc region; and
a scFv for the anti-4-1BB antibody linked by a peptide bond or a peptide linker sequence to the C-terminus of the immunoglobulin Fc region, wherein the scFv for the anti-4-1BB antibody comprises an amino acid sequence having 95% or more sequence identity to an amino acid sequence comprising SEQ ID NO: 17 and 18 linked by a peptide bond or a peptide linker sequence.

46. The bispecific antibody of claim 45, wherein the immunoglobulin Fc region comprises an amino acid sequence having 95% or more sequence identity to SEQ ID NO: 10 or SEQ ID NO: 16.

47. The bispecific antibody of claim 45, wherein the PD-1 polypeptide or the scFv or both are linked to the immunoglobulin Fc region by a peptide linker selected from the group consisting of SEQ ID NO: 19, SEQ ID NO: 20, and SEQ ID NO: 21.

48. The bispecific antibody of claim 45, wherein the scFv for the anti-4-1BB antibody comprises a sequence that is at least 90% identical to SEQ ID NO: 22 or SEQ ID NO:23.

49. The bispecific antibody of claim 45, wherein the scFv for the anti-4-1BB antibody comprises SEQ ID NO: 22 or SEQ ID NO: 23.

50. The bispecific antibody of claim 45, wherein the bispecific antibody has increased binding affinity to a PD-L1 molecule as compared to a wild-type PD-1 polypeptide and specific binding affinity to 4-1BB.

51. A pharmaceutical composition
comprising: the bispecific antibody of claim 45; and
a pharmaceutically acceptable carrier.

52. A method of treating a disease or a condition in a subject in need thereof, the method comprising:
administering to the subject the pharmaceutical composition of claim 51, thereby treating a disease or a condition.

53. The method of claim 52, wherein the subject has cancer.

54. The method of claim 53, wherein the cancer is selected from a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, and prostate cancer.

55. The method of claim 54, wherein when the pharmaceutical composition comprises said fusion protein, decreased or no antibody-dependent cellular cytotoxicity (ADCC) and/or complement-dependent cytotoxicity (CDC) effects are observed.

56. The method of claim 54, wherein when the pharmaceutical composition comprises said fusion protein, decreased or no hepatotoxicity is observed.

* * * * *

SEQUENCE LISTING

```
<160> NUMBER OF SEQ ID NOS: 23

<210> SEQ ID NO 1
<211> LENGTH: 447
<212> TYPE: DNA
<213> ORGANISM: Homo sapiens

<400> SEQUENCE: 1
tttttggatt ctccagaccg gccttggaac ccgcccacgt ttagccctgc tcttttggta      60
gttacagagg gggacaacgc cacattcacc tgcagcttct ctaatacgtc cgagagcttt     120
gtactgaatt ggtatagaat gagtccatct aatcagacag ataaattggc tgccttccct     180
gaagacagga gtcagccggg tcaggactgc agattccgcg ttacgcaact cccaaatggt     240
cgagactttc atatgtcagt tgttcgggcg aggagaaatg atagcggtac ttacctgtgc     300
ggcgcgatat ctctcgcacc aaaagcacag attaaagagt ctctccgggc tgaactccgc     360
gtgacagaaa ggcgagccga ggtaccaacg gcgcacccat caccgagtcc tagacctgcg     420
ggccaattcc agactttggt tgtcgga                                         447

<210> SEQ ID NO 2
<211> LENGTH: 149
<212> TYPE: PRT
<213> ORGANISM: Homo sapiens

<400> SEQUENCE: 2

Phe Leu Asp Ser Pro Asp Arg Pro Trp Asn Pro Pro Thr Phe Ser Pro
1               5                   10                  15

Ala Leu Leu Val Val Thr Glu Gly Asp Asn Ala Thr Phe Thr Cys Ser
            20                  25                  30

Phe Ser Asn Thr Ser Glu Ser Phe Val Leu Asn Trp Tyr Arg Met Ser
        35                  40                  45

Pro Ser Asn Gln Thr Asp Lys Leu Ala Ala Phe Pro Glu Asp Arg Ser
    50                  55                  60

Gln Pro Gly Gln Asp Cys Arg Phe Arg Val Thr Gln Leu Pro Asn Gly
65                  70                  75                  80

Arg Asp Phe His Met Ser Val Val Arg Ala Arg Arg Asn Asp Ser Gly
                85                  90                  95

Thr Tyr Leu Cys Gly Ala Ile Ser Leu Ala Pro Lys Ala Gln Ile Lys
            100                 105                 110

Glu Ser Leu Arg Ala Glu Leu Arg Val Thr Glu Arg Arg Ala Glu Val
            115                 120                 125
```

-continued

```
Pro Thr Ala His Pro Ser Pro Ser Pro Arg Pro Ala Gly Gln Phe Gln
    130                 135                 140

Thr Leu Val Val Gly
145

<210> SEQ ID NO 3
<211> LENGTH: 447
<212> TYPE: DNA
<213> ORGANISM: Artificial Sequence
<220> FEATURE:
<223> OTHER INFORMATION: PD-1 polypeptide variant PD-1.m7

<400> SEQUENCE: 3
tttctggagt cacccgaccg cccttggaac gcacctacct tttccccggc cctcttgctg      60
gtcgcagaag gagataacgc cactttcaca tgcagcttta gtaacgcctc cgaatctttt     120
catgtagttt ggcacagaga aagcccctcc ggacaaaccg acaccttggc tgcgtttccc     180
gaagaccgaa gtcaaccagg gcaggactgc cggttccgcg taacacggct gccaaacggt     240
agggacttcc acatgtcagt ggttcgagca cgccggaacg acagcgggac gtatgtctgc     300
ggagtcatta gccttgcccc gaagatacag attaaagaaa gtcttggggc agaacttcga     360
gtcaccgagc gcagggccga ggtcccaacg gcacatccca gtcctagtcc acggcccgcc     420
ggtcaatttc agacccttgt agtgggc                                         447

<210> SEQ ID NO 4
<211> LENGTH: 149
<212> TYPE: PRT
<213> ORGANISM: Artificial Sequence
<220> FEATURE:
<223> OTHER INFORMATION: PD-1 polypeptide variant PD-1.m7

<400> SEQUENCE: 4

Phe Leu Glu Ser Pro Asp Arg Pro Trp Asn Ala Pro Thr Phe Ser Pro
1               5                  10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
    50                  55                  60

Gln Pro Gly Gln Asp Cys Arg Phe Arg Val Thr Arg Leu Pro Asn Gly
65                  70                  75                  80

Arg Asp Phe His Met Ser Val Val Arg Ala Arg Arg Asn Asp Ser Gly
                85                  90                  95

Thr Tyr Val Cys Gly Val Ile Ser Leu Ala Pro Lys Ile Gln Ile Lys
            100                 105                 110

Glu Ser Leu Gly Ala Glu Leu Arg Val Thr Glu Arg Arg Ala Glu Val
        115                 120                 125

Pro Thr Ala His Pro Ser Pro Ser Pro Arg Pro Ala Gly Gln Phe Gln
    130                 135                 140

Thr Leu Val Val Gly
145

<210> SEQ ID NO 5
<211> LENGTH: 447
<212> TYPE: DNA
<213> ORGANISM: Artificial Sequence
<220> FEATURE:
<223> OTHER INFORMATION: PD-1 polypeptide variant PD-1.m8
```

-continued

<400> SEQUENCE: 5

```
tttttggaaa gtcccgatcg gccttggaac gctcccacat ttagcccggc cctgcttttg      60
gttgctgaag gcgataacgc cactttaca tgcagtttca gcaacgcctc tgaaagtttc     120
catgtagtgt ggcaccgcga gtctccaagt gggcaaacag atacccttgc agctttcccg     180
gaagatagga gtcagccagg gcaggatcac cggtttagag tcactcgcct ccccaatggt     240
agagattttc acatgagcgt cgttcgagct cagagaaacg atagtggcac atacgtttgt     300
ggcgtaatat ctctcgcccc gaagatccag attaaagagt cccttggcgc ggagctgaga     360
gtcaccgaga ggcgagctga ggtgcctaca gctcatccta gcccgagccc aaggccagct     420
ggacagttcc aaactttggt tgtaggc                                        447
```

<210> SEQ ID NO 6
<211> LENGTH: 149
<212> TYPE: PRT
<213> ORGANISM: Artificial Sequence
<220> FEATURE:
<223> OTHER INFORMATION: PD-1 polypeptide variant PD-1.m8

<400> SEQUENCE: 6

```
Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
    50                  55                  60

Gln Pro Gly Gln Asp His Arg Phe Arg Val Thr Arg Leu Pro Asn Gly
65                  70                  75                  80

Arg Asp Phe His Met Ser Val Val Arg Ala Gln Arg Asn Asp Ser Gly
                85                  90                  95

Thr Tyr Val Cys Gly Val Ile Ser Leu Ala Pro Lys Ile Gln Ile Lys
            100                 105                 110

Glu Ser Leu Gly Ala Glu Leu Arg Val Thr Glu Arg Arg Ala Glu Val
        115                 120                 125

Pro Thr Ala His Pro Ser Pro Ser Pro Arg Pro Ala Gly Gln Phe Gln
    130                 135                 140

Thr Leu Val Val Gly
145
```

<210> SEQ ID NO 7
<211> LENGTH: 447
<212> TYPE: DNA
<213> ORGANISM: Artificial Sequence
<220> FEATURE:
<223> OTHER INFORMATION: PD-1 polypeptide variant euPD-1

<400> SEQUENCE: 7

```
tttctcgaat caccggacag accctggaat gcgcccacat tctcaccagc acttttgctg      60
gtagcagagg gcgataatgc tacattcacg tgttccttca gtaatgcaag cgagtcattt     120
catgtggttt ggcatcgaga gtcacctagt gggcagactg atacacttgc cgcattcccg     180
gaagatcgct cccagccagg tcaggatcac cggttcaggg taacccgact gccgaatggg     240
cgcgatttcc atatgagcgt tgtccgggcg caacggaacg atagtggaac atacgtgtgt     300
```

```
ggcgtaatat ccctcgctcc caaaatacaa ataaaggagt ctctgagagc agagctgaga    360
gtgacagaac gacgggcgga agttcccacg gctcatccgt caccaagtcc gcgccccgca    420
ggccaatttc aaacgctcgt cgtaggc                                        447
```

<210> SEQ ID NO 8
<211> LENGTH: 149
<212> TYPE: PRT
<213> ORGANISM: Artificial Sequence
<220> FEATURE:
<223> OTHER INFORMATION: PD-1 polypeptide variant euPD-1

<400> SEQUENCE: 8

```
Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
    50                  55                  60

Gln Pro Gly Gln Asp His Arg Phe Arg Val Thr Arg Leu Pro Asn Gly
65                  70                  75                  80

Arg Asp Phe His Met Ser Val Val Arg Ala Gln Arg Asn Asp Ser Gly
                85                  90                  95

Thr Tyr Val Cys Gly Val Ile Ser Leu Ala Pro Lys Ile Gln Ile Lys
            100                 105                 110

Glu Ser Leu Arg Ala Glu Leu Arg Val Thr Glu Arg Arg Ala Glu Val
        115                 120                 125

Pro Thr Ala His Pro Ser Pro Ser Pro Arg Pro Ala Gly Gln Phe Gln
    130                 135                 140

Thr Leu Val Val Gly
145
```

<210> SEQ ID NO 9
<211> LENGTH: 720
<212> TYPE: DNA
<213> ORGANISM: Artificial Sequence
<220> FEATURE:
<223> OTHER INFORMATION: Fc (207-230 IMGT allele IGHG1*03, 231- 457 IMGT
      allele IGHG2*01)

<400> SEQUENCE: 9

```
agcaacacta aagtcgacaa gcgagtagaa ccgaaatcat gcgacaaaac acatacgtgc     60
cctccctgcc cagcaccacc tgtcgcgggc ccctctgttt tcctgtttcc acccaagcca    120
aaggacacat tgatgatttc ccggactcct gaagtcacct gcgtggtagt agatgtatca    180
catgaagatc cagaagtcca gttcaactgg tatgtggacg gagtagaggt acataatgcc    240
aagaccaaac cacgggaaga gcagttcaac agtactttcc gggtagttag cgttttgact    300
gtcgtacacc aagactggct taatggaaaa gaatacaagt gtaaggtaag caacaagggc    360
ctgccggctc cgatagagaa aaccattagc aagacaaagg gccaaccacg cgaaccccag    420
gtatataccc tcccaccgtc ccgcgaggag atgactaaga tcaagtttc tctcacgtgc    480 ttggtaaagg gcttctatcc gagcgatata gccgtggagt gggagtctaa tggtcagccc    540
gaaaacaatt acaaaactac gcctcctatg ctggacagtg atgggagctt ctttctttac    600
agtaagctta ccgtggacaa gtctcggtgg caacaaggaa atgttttag ttgttctgta    660
```

-continued

```
atgcatgaag cacttcataa ccattacacc cagaaaagtc tgagcttgtc cccgggaaaa      720
```

```
<210> SEQ ID NO 10
<211> LENGTH: 240
<212> TYPE: PRT
<213> ORGANISM: Artificial Sequence
<220> FEATURE:
<223> OTHER INFORMATION: Fc (207-230 IMGT allele IGHG1*03, 231- 457 IMGT
      allele IGHG2*01)

<400> SEQUENCE: 10

Ser Asn Thr Lys Val Asp Lys Arg Val Glu Pro Lys Ser Cys Asp Lys
1               5                   10                  15

Thr His Thr Cys Pro Pro Cys Pro Ala Pro Val Ala Gly Pro Ser
            20                  25                  30

Val Phe Leu Phe Pro Pro Lys Pro Lys Asp Thr Leu Met Ile Ser Arg
        35                  40                  45

Thr Pro Glu Val Thr Cys Val Val Val Asp Val Ser His Glu Asp Pro
    50                  55                  60

Glu Val Gln Phe Asn Trp Tyr Val Asp Gly Val Glu Val His Asn Ala
65                  70                  75                  80

Lys Thr Lys Pro Arg Glu Glu Gln Phe Asn Ser Thr Phe Arg Val Val
                85                  90                  95

Ser Val Leu Thr Val Val His Gln Asp Trp Leu Asn Gly Lys Glu Tyr
            100                 105                 110

Lys Cys Lys Val Ser Asn Lys Gly Leu Pro Ala Pro Ile Glu Lys Thr
        115                 120                 125

Ile Ser Lys Thr Lys Gly Gln Pro Arg Glu Pro Gln Val Tyr Thr Leu
    130                 135                 140

Pro Pro Ser Arg Glu Glu Met Thr Lys Asn Gln Val Ser Leu Thr Cys
145                 150                 155                 160

Leu Val Lys Gly Phe Tyr Pro Ser Asp Ile Ala Val Glu Trp Glu Ser
                165                 170                 175

Asn Gly Gln Pro Glu Asn Asn Tyr Lys Thr Thr Pro Pro Met Leu Asp
            180                 185                 190

Ser Asp Gly Ser Phe Phe Leu Tyr Ser Lys Leu Thr Val Asp Lys Ser
        195                 200                 205

Arg Trp Gln Gln Gly Asn Val Phe Ser Cys Ser Val Met His Glu Ala
    210                 215                 220

Leu His Asn His Tyr Thr Gln Lys Ser Leu Ser Leu Ser Pro Gly Lys
225                 230                 235                 240

<210> SEQ ID NO 11
<211> LENGTH: 288
<212> TYPE: PRT
<213> ORGANISM: Homo Sapience

<400> SEQUENCE: 11

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
```

```
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 12
<211> LENGTH: 641
<212> TYPE: PRT
<213> ORGANISM: Artificial Sequence
<220> FEATURE:
<223> OTHER INFORMATION: euPD-1 x 94kvt HLC 218

<400> SEQUENCE: 12

Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
                20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
        50                  55                  60

Gln Pro Gly Gln Asp His Arg Phe Arg Val Thr Arg Leu Pro Asn Gly
65                  70                  75                  80

Arg Asp Phe His Met Ser Val Val Arg Ala Gln Arg Asn Asp Ser Gly
                85                  90                  95

Thr Tyr Val Cys Gly Val Ile Ser Leu Ala Pro Lys Ile Gln Ile Lys
                100                 105                 110

Glu Ser Leu Arg Ala Glu Leu Arg Val Thr Glu Arg Arg Ala Glu Val
        115                 120                 125

Pro Thr Ala His Pro Ser Pro Ser Pro Arg Pro Ala Gly Gln Phe Gln
        130                 135                 140

Thr Leu Val Val Gly Ala Ser Gly Gly Gly Gly Ser Gly Gly Gly Gly
```

```
145               150               155               160

Ser Asp Lys Thr His Thr Cys Pro Pro Cys Pro Ala Pro Glu Ala Ala
              165               170               175

Gly Gly Pro Ser Val Phe Leu Phe Pro Pro Lys Pro Lys Asp Thr Leu
              180               185               190

Met Ile Ser Arg Thr Pro Glu Val Thr Cys Val Val Val Asp Val Ser
              195               200               205

His Glu Asp Pro Glu Val Lys Phe Asn Trp Tyr Val Asp Gly Val Glu
      210               215               220

Val His Asn Ala Lys Thr Lys Pro Arg Glu Glu Gln Tyr Asn Ser Thr
225               230               235               240

Tyr Arg Val Val Ser Val Leu Thr Val Leu His Gln Asp Trp Leu Asn
                  245               250               255

Gly Lys Glu Tyr Lys Cys Ala Val Ser Asn Lys Ala Leu Pro Ala Pro
              260               265               270

Ile Glu Lys Thr Ile Ser Lys Ala Lys Gly Gln Pro Arg Glu Pro Gln
              275               280               285

Val Tyr Thr Leu Pro Pro Ser Arg Glu Glu Met Thr Lys Asn Gln Val
      290               295               300

Ser Leu Thr Cys Leu Val Lys Gly Phe Tyr Pro Ser Asp Ile Ala Val
305               310               315               320

Glu Trp Glu Ser Asn Gly Gln Pro Glu Asn Asn Tyr Lys Thr Thr Pro
                  325               330               335

Pro Val Leu Asp Ser Asp Gly Ser Phe Phe Leu Tyr Ser Lys Leu Thr
              340               345               350

Val Asp Lys Ser Arg Trp Gln Gln Gly Asn Val Phe Ser Cys Ser Val
      355               360               365

Met His Glu Ala Leu His Asn His Tyr Thr Gln Lys Ser Leu Ser Leu
      370               375               380

Ser Pro Gly Gly Gly Gly Ser Gly Gly Gly Gly Ser Gln Val Gln
385               390               395               400

Leu Val Gln Ser Gly Ala Glu Val Lys Lys Pro Gly Ala Ser Val Lys
              405               410               415

Leu Ser Cys Lys Ala Ser Gly Tyr Thr Phe Ser Ser Tyr Trp Met His
              420               425               430

Trp Val Arg Gln Ala Pro Gly Gln Gly Leu Glu Trp Ile Gly Glu Ile
      435               440               445

Asn Pro Gly Asn Gly His Thr Asn Tyr Asn Glu Lys Phe Lys Ser Arg
      450               455               460

Val Thr Met Thr Arg Asp Thr Ser Thr Ser Thr Ala Tyr Met Glu Leu
465               470               475               480

Ser Ser Leu Arg Ser Glu Asp Thr Ala Val Tyr Tyr Cys Ala Arg Ser
              485               490               495

Phe Lys Thr Ala Arg Ala Phe Ala Tyr Trp Gly Gln Gly Thr Leu Val
              500               505               510

Thr Val Ser Ser Gly Ser Thr Ser Gly Ser Gly Lys Pro Gly Ser Gly
          515               520               525

Glu Gly Ser Thr Lys Gly Asp Ile Val Met Thr Gln Ser Pro Ala Phe
      530               535               540

Leu Ser Val Thr Pro Gly Glu Lys Val Thr Ile Thr Cys Arg Ala Ser
545               550               555               560

Gln Thr Ile Ser Asp Tyr Leu His Trp Tyr Gln Gln Lys Pro Asp Gln
              565               570               575
```

-continued

```
Ala Pro Lys Leu Leu Ile Lys Tyr Ala Ser Gln Ser Ile Ser Gly Ile
            580                 585                 590

Pro Ser Arg Phe Ser Gly Ser Gly Ser Gly Thr Asp Phe Thr Phe Thr
            595                 600                 605

Ile Ser Ser Leu Glu Ala Glu Asp Ala Ala Thr Tyr Tyr Cys Gln Asp
            610                 615                 620

Gly His Ser Trp Pro Pro Thr Phe Gly Gln Gly Thr Lys Leu Glu Ile
625                 630                 635                 640

Lys

<210> SEQ ID NO 13
<211> LENGTH: 805
<212> TYPE: PRT
<213> ORGANISM: Artificial Sequence
<220> FEATURE:
<223> OTHER INFORMATION: euPD-1.2 x 94kvt HLC 218

<400> SEQUENCE: 13

Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
            35                  40                  45

Pro Ser Gly Gln Thr Asp Thr Leu Ala Ala Phe Pro Glu Asp Arg Ser
            50                  55                  60

Gln Pro Gly Gln Asp His Arg Phe Arg Val Thr Arg Leu Pro Asn Gly
65                  70                  75                  80

Arg Asp Phe His Met Ser Val Val Arg Ala Gln Arg Asn Asp Ser Gly
                85                  90                  95

Thr Tyr Val Cys Gly Val Ile Ser Leu Ala Pro Lys Ile Gln Ile Lys
            100                 105                 110

Glu Ser Leu Arg Ala Glu Leu Arg Val Thr Glu Arg Arg Ala Glu Val
            115                 120                 125

Pro Thr Ala His Pro Ser Pro Ser Pro Arg Pro Ala Gly Gln Phe Gln
            130                 135                 140

Thr Leu Val Val Gly Gly Gly Gly Ser Gly Gly Gly Gly Ser Gly
145                 150                 155                 160

Gly Gly Gly Ser Phe Leu Glu Ser Pro Asp Arg Pro Trp Asn Ala Pro
                165                 170                 175

Thr Phe Ser Pro Ala Leu Leu Leu Val Ala Glu Gly Asp Asn Ala Thr
                180                 185                 190

Phe Thr Cys Ser Phe Ser Asn Ala Ser Glu Ser Phe His Val Val Trp
                195                 200                 205

His Arg Glu Ser Pro Ser Gly Gln Thr Asp Thr Leu Ala Ala Phe Pro
            210                 215                 220

Glu Asp Arg Ser Gln Pro Gly Gln Asp His Arg Phe Arg Val Thr Arg
225                 230                 235                 240

Leu Pro Asn Gly Arg Asp Phe His Met Ser Val Val Arg Ala Gln Arg
                245                 250                 255

Asn Asp Ser Gly Thr Tyr Val Cys Gly Val Ile Ser Leu Ala Pro Lys
            260                 265                 270

Ile Gln Ile Lys Glu Ser Leu Arg Ala Glu Leu Arg Val Thr Glu Arg
            275                 280                 285
```

-continued

```
Arg Ala Glu Val Pro Thr Ala His Pro Ser Pro Ser Pro Arg Pro Ala
    290                 295                 300

Gly Gln Phe Gln Thr Leu Val Val Gly Ala Ser Gly Gly Gly Gly Ser
305                 310                 315                 320

Gly Gly Gly Gly Ser Asp Lys Thr His Thr Cys Pro Pro Cys Pro Ala
                325                 330                 335

Pro Glu Ala Ala Gly Gly Pro Ser Val Phe Leu Phe Pro Pro Lys Pro
                340                 345                 350

Lys Asp Thr Leu Met Ile Ser Arg Thr Pro Glu Val Thr Cys Val Val
            355                 360                 365

Val Asp Val Ser His Glu Asp Pro Glu Val Lys Phe Asn Trp Tyr Val
    370                 375                 380

Asp Gly Val Glu Val His Asn Ala Lys Thr Lys Pro Arg Glu Glu Gln
385                 390                 395                 400

Tyr Asn Ser Thr Tyr Arg Val Val Ser Val Leu Thr Val Leu His Gln
                405                 410                 415

Asp Trp Leu Asn Gly Lys Glu Tyr Lys Cys Ala Val Ser Asn Lys Ala
            420                 425                 430

Leu Pro Ala Pro Ile Glu Lys Thr Ile Ser Lys Ala Lys Gly Gln Pro
            435                 440                 445

Arg Glu Pro Gln Val Tyr Thr Leu Pro Pro Ser Arg Glu Glu Met Thr
    450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Thr Thr Pro Pro Val Leu Asp Ser Asp Gly Ser Phe Phe Leu Tyr
                500                 505                 510

Ser Lys Leu Thr Val Asp Lys Ser Arg Trp Gln Gln Gly Asn Val Phe
            515                 520                 525

Ser Cys Ser Val Met His Glu Ala Leu His Asn His Tyr Thr Gln Lys
    530                 535                 540

Ser Leu Ser Leu Ser Pro Gly Gly Gly Gly Ser Gly Gly Gly Gly
545                 550                 555                 560

Ser Gln Val Gln Leu Val Gln Ser Gly Ala Glu Val Lys Lys Pro Gly
                565                 570                 575

Ala Ser Val Lys Leu Ser Cys Lys Ala Ser Gly Tyr Thr Phe Ser Ser
            580                 585                 590

Tyr Trp Met His Trp Val Arg Gln Ala Pro Gly Gln Gly Leu Glu Trp
            595                 600                 605

Ile Gly Glu Ile Asn Pro Gly Asn Gly His Thr Asn Tyr Asn Glu Lys
    610                 615                 620

Phe Lys Ser Arg Val Thr Met Thr Arg Asp Thr Ser Thr Ser Thr Ala
625                 630                 635                 640

Tyr Met Glu Leu Ser Ser Leu Arg Ser Glu Asp Thr Ala Val Tyr Tyr
                645                 650                 655

Cys Ala Arg Ser Phe Lys Thr Ala Arg Ala Phe Ala Tyr Trp Gly Gln
            660                 665                 670

Gly Thr Leu Val Thr Val Ser Ser Gly Ser Thr Ser Gly Ser Gly Lys
            675                 680                 685

Pro Gly Ser Gly Glu Gly Ser Thr Lys Gly Asp Ile Val Met Thr Gln
    690                 695                 700

Ser Pro Ala Phe Leu Ser Val Thr Pro Gly Glu Lys Val Thr Ile Thr
```

-continued

```
705             710             715             720

Cys Arg Ala Ser Gln Thr Ile Ser Asp Tyr Leu His Trp Tyr Gln Gln
                725             730             735

Lys Pro Asp Gln Ala Pro Lys Leu Leu Ile Lys Tyr Ala Ser Gln Ser
            740             745             750

Ile Ser Gly Ile Pro Ser Arg Phe Ser Gly Ser Gly Ser Gly Thr Asp
            755             760             765

Phe Thr Phe Thr Ile Ser Ser Leu Glu Ala Glu Asp Ala Ala Thr Tyr
        770             775             780

Tyr Cys Gln Asp Gly His Ser Trp Pro Pro Thr Phe Gly Gln Gly Thr
785             790             795             800

Lys Leu Glu Ile Lys
                805
```

```
<210> SEQ ID NO 14
<211> LENGTH: 641
<212> TYPE: PRT
<213> ORGANISM: Artificial Sequence
<220> FEATURE:
<223> OTHER INFORMATION: euPD-1 x 94kvt LHC 218

<400> SEQUENCE: 14

Phe Leu Glu Ser Pro Asp Arg Pro Trp Asn Ala Pro Thr Phe Ser Pro
1               5               10              15

Ala Leu Leu Leu Val Ala Glu Gly Asp Asn Ala Thr Phe Thr Cys Ser
            20              25              30

Phe Ser Asn Ala Ser Glu Ser Phe His Val Val Trp His Arg Glu Ser
            35              40              45

Pro Ser Gly Gln Thr Asp Thr Leu Ala Ala Phe Pro Glu Asp Arg Ser
        50              55              60

Gln Pro Gly Gln Asp His Arg Phe Arg Val Thr Arg Leu Pro Asn Gly
65              70              75              80

Arg Asp Phe His Met Ser Val Val Arg Ala Gln Arg Asn Asp Ser Gly
                85              90              95

Thr Tyr Val Cys Gly Val Ile Ser Leu Ala Pro Lys Ile Gln Ile Lys
            100             105             110

Glu Ser Leu Arg Ala Glu Leu Arg Val Thr Glu Arg Arg Ala Glu Val
        115             120             125

Pro Thr Ala His Pro Ser Pro Ser Pro Arg Pro Ala Gly Gln Phe Gln
    130             135             140

Thr Leu Val Val Gly Ala Ser Gly Gly Gly Gly Ser Gly Gly Gly Gly
145             150             155             160

Ser Asp Lys Thr His Thr Cys Pro Pro Cys Pro Ala Pro Glu Ala Ala
            165             170             175

Gly Gly Pro Ser Val Phe Leu Phe Pro Pro Lys Pro Lys Asp Thr Leu
            180             185             190

Met Ile Ser Arg Thr Pro Glu Val Thr Cys Val Val Val Asp Val Ser
            195             200             205

His Glu Asp Pro Glu Val Lys Phe Asn Trp Tyr Val Asp Gly Val Glu
        210             215             220

Val His Asn Ala Lys Thr Lys Pro Arg Glu Glu Gln Tyr Asn Ser Thr
225             230             235             240

Tyr Arg Val Val Ser Val Leu Thr Val Leu His Gln Asp Trp Leu Asn
            245             250             255

Gly Lys Glu Tyr Lys Cys Ala Val Ser Asn Lys Ala Leu Pro Ala Pro
```

-continued

```
                260                265                270
Ile Glu Lys Thr Ile Ser Lys Ala Lys Gly Gln Pro Arg Glu Pro Gln
        275                280                285
Val Tyr Thr Leu Pro Pro Ser Arg Glu Glu Met Thr Lys Asn Gln Val
        290                295                300
Ser Leu Thr Cys Leu Val Lys Gly Phe Tyr Pro Ser Asp Ile Ala Val
305                310                315                320
Glu Trp Glu Ser Asn Gly Gln Pro Glu Asn Asn Tyr Lys Thr Thr Pro
                325                330                335
Pro Val Leu Asp Ser Asp Gly Ser Phe Phe Leu Tyr Ser Lys Leu Thr
                340                345                350
Val Asp Lys Ser Arg Trp Gln Gln Gly Asn Val Phe Ser Cys Ser Val
        355                360                365
Met His Glu Ala Leu His Asn His Tyr Thr Gln Lys Ser Leu Ser Leu
        370                375                380
Ser Pro Gly Gly Gly Gly Gly Ser Gly Gly Gly Gly Ser Asp Ile Val
385                390                395                400
Met Thr Gln Ser Pro Ala Phe Leu Ser Val Thr Pro Gly Glu Lys Val
                405                410                415
Thr Ile Thr Cys Arg Ala Ser Gln Thr Ile Ser Asp Tyr Leu His Trp
                420                425                430
Tyr Gln Gln Lys Pro Asp Gln Ala Pro Lys Leu Leu Ile Lys Tyr Ala
        435                440                445
Ser Gln Ser Ile Ser Gly Ile Pro Ser Arg Phe Ser Gly Ser Gly Ser
        450                455                460
Gly Thr Asp Phe Thr Phe Thr Ile Ser Ser Leu Glu Ala Glu Asp Ala
465                470                475                480
Ala Thr Tyr Tyr Cys Gln Asp Gly His Ser Trp Pro Pro Thr Phe Gly
                485                490                495
Gln Gly Thr Lys Leu Glu Ile Lys Gly Ser Thr Ser Gly Ser Gly Lys
                500                505                510
Pro Gly Ser Gly Glu Gly Ser Thr Lys Gly Gln Val Gln Leu Val Gln
        515                520                525
Ser Gly Ala Glu Val Lys Lys Pro Gly Ala Ser Val Lys Leu Ser Cys
        530                535                540
Lys Ala Ser Gly Tyr Thr Phe Ser Ser Tyr Trp Met His Trp Val Arg
545                550                555                560
Gln Ala Pro Gly Gln Gly Leu Glu Trp Ile Gly Glu Ile Asn Pro Gly
                565                570                575
Asn Gly His Thr Asn Tyr Asn Glu Lys Phe Lys Ser Arg Val Thr Met
                580                585                590
Thr Arg Asp Thr Ser Thr Ser Thr Ala Tyr Met Glu Leu Ser Ser Leu
        595                600                605
Arg Ser Glu Asp Thr Ala Val Tyr Tyr Cys Ala Arg Ser Phe Lys Thr
        610                615                620
Ala Arg Ala Phe Ala Tyr Trp Gly Gln Gly Thr Leu Val Thr Val Ser
625                630                635                640
Ser
```

<210> SEQ ID NO 15
<211> LENGTH: 805
<212> TYPE: PRT
<213> ORGANISM: Artificial Sequence
<220> FEATURE:

<223> OTHER INFORMATION: euPD-1.2 x 94kvt LHC 218

<400> SEQUENCE: 15

```
Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
    50                  55                  60

Gln Pro Gly Gln Asp His Arg Phe Arg Val Thr Arg Leu Pro Asn Gly
65                  70                  75                  80

Arg Asp Phe His Met Ser Val Val Arg Ala Gln Arg Asn Asp Ser Gly
                85                  90                  95

Thr Tyr Val Cys Gly Val Ile Ser Leu Ala Pro Lys Ile Gln Ile Lys
            100                 105                 110

Glu Ser Leu Arg Ala Glu Leu Arg Val Thr Glu Arg Arg Ala Glu Val
        115                 120                 125

Pro Thr Ala His Pro Ser Pro Ser Pro Arg Pro Ala Gly Gln Phe Gln
    130                 135                 140

Thr Leu Val Val Gly Gly Gly Gly Ser Gly Gly Gly Gly Ser Gly
145                 150                 155                 160

Gly Gly Gly Ser Phe Leu Glu Ser Pro Asp Arg Pro Trp Asn Ala Pro
                165                 170                 175

Thr Phe Ser Pro Ala Leu Leu Leu Val Ala Glu Gly Asp Asn Ala Thr
                180                 185                 190

Phe Thr Cys Ser Phe Ser Asn Ala Ser Glu Ser Phe His Val Val Trp
            195                 200                 205

His Arg Glu Ser Pro Ser Gly Gln Thr Asp Thr Leu Ala Ala Phe Pro
    210                 215                 220

Glu Asp Arg Ser Gln Pro Gly Gln Asp His Arg Phe Arg Val Thr Arg
225                 230                 235                 240

Leu Pro Asn Gly Arg Asp Phe His Met Ser Val Val Arg Ala Gln Arg
                245                 250                 255

Asn Asp Ser Gly Thr Tyr Val Cys Gly Val Ile Ser Leu Ala Pro Lys
            260                 265                 270

Ile Gln Ile Lys Glu Ser Leu Arg Ala Glu Leu Arg Val Thr Glu Arg
        275                 280                 285

Arg Ala Glu Val Pro Thr Ala His Pro Ser Pro Ser Pro Arg Pro Ala
    290                 295                 300

Gly Gln Phe Gln Thr Leu Val Val Gly Ala Ser Gly Gly Gly Gly Ser
305                 310                 315                 320

Gly Gly Gly Gly Ser Asp Lys Thr His Thr Cys Pro Pro Cys Pro Ala
                325                 330                 335

Pro Glu Ala Ala Gly Gly Pro Ser Val Phe Leu Phe Pro Pro Lys Pro
                340                 345                 350

Lys Asp Thr Leu Met Ile Ser Arg Thr Pro Glu Val Thr Cys Val Val
            355                 360                 365

Val Asp Val Ser His Glu Asp Pro Glu Val Lys Phe Asn Trp Tyr Val
    370                 375                 380

Asp Gly Val Glu Val His Asn Ala Lys Thr Lys Pro Arg Glu Glu Gln
385                 390                 395                 400
```

-continued

```
Tyr Asn Ser Thr Tyr Arg Val Val Ser Val Leu Thr Val Leu His Gln
                405             410             415

Asp Trp Leu Asn Gly Lys Glu Tyr Lys Cys Ala Val Ser Asn Lys Ala
        420             425             430

Leu Pro Ala Pro Ile Glu Lys Thr Ile Ser Lys Ala Lys Gly Gln Pro
        435             440             445

Arg Glu Pro Gln Val Tyr Thr Leu Pro Pro Ser Arg Glu Glu Met Thr
    450             455             460

Lys Asn Gln Val Ser Leu Thr Cys Leu Val Lys Gly Phe Tyr Pro Ser
465             470             475             480

Asp Ile Ala Val Glu Trp Glu Ser Asn Gly Gln Pro Glu Asn Asn Tyr
            485             490             495

Lys Thr Thr Pro Pro Val Leu Asp Ser Asp Gly Ser Phe Phe Leu Tyr
            500             505             510

Ser Lys Leu Thr Val Asp Lys Ser Arg Trp Gln Gln Gly Asn Val Phe
        515             520             525

Ser Cys Ser Val Met His Glu Ala Leu His Asn His Tyr Thr Gln Lys
        530             535             540

Ser Leu Ser Leu Ser Pro Gly Gly Gly Gly Gly Ser Gly Gly Gly Gly
545             550             555             560

Ser Asp Ile Val Met Thr Gln Ser Pro Ala Phe Leu Ser Val Thr Pro
            565             570             575

Gly Glu Lys Val Thr Ile Thr Cys Arg Ala Ser Gln Thr Ile Ser Asp
            580             585             590

Tyr Leu His Trp Tyr Gln Gln Lys Pro Asp Gln Ala Pro Lys Leu Leu
        595             600             605

Ile Lys Tyr Ala Ser Gln Ser Ile Ser Gly Ile Pro Ser Arg Phe Ser
    610             615             620

Gly Ser Gly Ser Gly Thr Asp Phe Thr Phe Thr Ile Ser Ser Leu Glu
625             630             635             640

Ala Glu Asp Ala Ala Thr Tyr Tyr Cys Gln Asp Gly His Ser Trp Pro
            645             650             655

Pro Thr Phe Gly Gln Gly Thr Lys Leu Glu Ile Lys Gly Ser Thr Ser
            660             665             670

Gly Ser Gly Lys Pro Gly Ser Gly Glu Gly Ser Thr Lys Gly Gln Val
        675             680             685

Gln Leu Val Gln Ser Gly Ala Glu Val Lys Lys Pro Gly Ala Ser Val
    690             695             700

Lys Leu Ser Cys Lys Ala Ser Gly Tyr Thr Phe Ser Ser Tyr Trp Met
705             710             715             720

His Trp Val Arg Gln Ala Pro Gly Gln Gly Leu Glu Trp Ile Gly Glu
            725             730             735

Ile Asn Pro Gly Asn Gly His Thr Asn Tyr Asn Glu Lys Phe Lys Ser
        740             745             750

Arg Val Thr Met Thr Arg Asp Thr Ser Thr Ser Thr Ala Tyr Met Glu
        755             760             765

Leu Ser Ser Leu Arg Ser Glu Asp Thr Ala Val Tyr Tyr Cys Ala Arg
    770             775             780

Ser Phe Lys Thr Ala Arg Ala Phe Ala Tyr Trp Gly Gln Gly Thr Leu
785             790             795             800

Val Thr Val Ser Ser
            805
```

```
<210> SEQ ID NO 16
<211> LENGTH: 226
<212> TYPE: PRT
<213> ORGANISM: Artificial Sequence
<220> FEATURE:
<223> OTHER INFORMATION: Fc

<400> SEQUENCE: 16

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Ala Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 17
<211> LENGTH: 119
<212> TYPE: PRT
<213> ORGANISM: Artificial Sequence
<220> FEATURE:
<223> OTHER INFORMATION: 94kvt VH

<400> SEQUENCE: 17

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
                20                  25                  30

Trp Met His Trp Val Arg Gln Ala Pro Gly Gln Gly Leu Glu Trp Ile
            35                  40                  45

Gly Glu Ile Asn Pro Gly Asn Gly His Thr Asn Tyr Asn Glu Lys Phe
        50                  55                  60

Lys Ser Arg Val Thr Met Thr Arg Asp Thr Ser Thr Ser Thr Ala Tyr
65                  70                  75                  80
```

-continued

```
Met Glu Leu Ser Ser Leu Arg Ser Glu Asp Thr Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: 94kvt VL

<400> SEQUENCE: 18

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Trp Pro Pro
                85                  90                  95

Thr Phe Gly Gln Gly Thr Lys Leu Glu Ile Lys
            100                 105

<210> SEQ ID NO 19
<211> LENGTH: 10
<212> TYPE: PRT
<213> ORGANISM: Artificial Sequence
<220> FEATURE:
<223> OTHER INFORMATION: (G4S)2

<400> SEQUENCE: 19

Gly Gly Gly Gly Ser Gly Gly Gly Gly Ser
1               5                   10

<210> SEQ ID NO 20
<211> LENGTH: 15
<212> TYPE: PRT
<213> ORGANISM: Artificial Sequence
<220> FEATURE:
<223> OTHER INFORMATION: (G4S)3

<400> SEQUENCE: 20

Gly Gly Gly Gly Ser Gly Gly Gly Gly Ser Gly Gly Gly Gly Ser
1               5                   10                  15

<210> SEQ ID NO 21
<211> LENGTH: 18
<212> TYPE: PRT
<213> ORGANISM: Artificial Sequence
<220> FEATURE:
<223> OTHER INFORMATION: 218

<400> SEQUENCE: 21

Gly Ser Thr Ser Gly Ser Gly Lys Pro Gly Ser Gly Glu Gly Ser Thr
1               5                   10                  15
```

-continued

```
Lys Gly

<210> SEQ ID NO 22
<211> LENGTH: 244
<212> TYPE: PRT
<213> ORGANISM: Artificial Sequence
<220> FEATURE:
<223> OTHER INFORMATION: 94kvt HLC 218

<400> SEQUENCE: 22

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser Gly Ser Thr Ser Gly Ser Gly Lys Pro
            115                 120                 125

Gly Ser Gly Glu Gly Ser Thr Lys Gly Asp Ile Val Met Thr Gln Ser
    130                 135                 140

Pro Ala Phe Leu Ser Val Thr Pro Gly Glu Lys Val Thr Ile Thr Cys
145                 150                 155                 160

Arg Ala Ser Gln Thr Ile Ser Asp Tyr Leu His Trp Tyr Gln Gln Lys
                165                 170                 175

Pro Asp Gln Ala Pro Lys Leu Leu Ile Lys Tyr Ala Ser Gln Ser Ile
            180                 185                 190

Ser Gly Ile Pro Ser Arg Phe Ser Gly Ser Gly Ser Gly Thr Asp Phe
            195                 200                 205

Thr Phe Thr Ile Ser Ser Leu Glu Ala Glu Asp Ala Ala Thr Tyr Tyr
    210                 215                 220

Cys Gln Asp Gly His Ser Trp Pro Pro Thr Phe Gly Gln Gly Thr Lys
225                 230                 235                 240

Leu Glu Ile Lys

<210> SEQ ID NO 23
<211> LENGTH: 244
<212> TYPE: PRT
<213> ORGANISM: Artificial Sequence
<220> FEATURE:
<223> OTHER INFORMATION: 94kvt LHC 218

<400> SEQUENCE: 23

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
```

-continued

```
       50                55                60

Ser Gly Ser Gly Thr Asp Phe Thr Phe Thr Ile Ser Ser Leu Glu Ala
65                70                75                80

Glu Asp Ala Ala Thr Tyr Tyr Cys Gln Asp Gly His Ser Trp Pro Pro
              85                90                95

Thr Phe Gly Gln Gly Thr Lys Leu Glu Ile Lys Gly Ser Thr Ser Gly
              100               105               110

Ser Gly Lys Pro Gly Ser Gly Glu Gly Ser Thr Lys Gly Gln Val Gln
              115               120               125

Leu Val Gln Ser Gly Ala Glu Val Lys Lys Pro Gly Ala Ser Val Lys
        130               135               140

Leu Ser Cys Lys Ala Ser Gly Tyr Thr Phe Ser Ser Tyr Trp Met His
145               150               155               160

Trp Val Arg Gln Ala Pro Gly Gln Gly Leu Glu Trp Ile Gly Glu Ile
              165               170               175

Asn Pro Gly Asn Gly His Thr Asn Tyr Asn Glu Lys Phe Lys Ser Arg
              180               185               190

Val Thr Met Thr Arg Asp Thr Ser Thr Ser Thr Ala Tyr Met Glu Leu
        195               200               205

Ser Ser Leu Arg Ser Glu Asp Thr Ala Val Tyr Tyr Cys Ala Arg Ser
        210               215               220

Phe Lys Thr Ala Arg Ala Phe Ala Tyr Trp Gly Gln Gly Thr Leu Val
225               230               235               240

Thr Val Ser Ser
```